United States Patent
Zelle et al.

(10) Patent No.: US 7,368,467 B2
(45) Date of Patent: May 6, 2008

(54) ION CHANNEL MODULATORS

(75) Inventors: Robert Zelle, Stow, MA (US); Vincent P. Galullo, South Grafton, MA (US); Hormoz Mazdiyasni, Douglas, MA (US)

(73) Assignee: Wyeth, Madison, NJ (US)

( * ) Notice: Subject to any disclaimer, the term of this patent is extended or adjusted under 35 U.S.C. 154(b) by 477 days.

(21) Appl. No.: 11/075,629

(22) Filed: Mar. 7, 2005

(65) Prior Publication Data

US 2005/0203159 A1 Sep. 15, 2005

Related U.S. Application Data

(60) Provisional application No. 60/551,371, filed on Mar. 8, 2004.

(51) Int. Cl.
*A61K 31/4184* (2006.01)
*C07D 233/54* (2006.01)
*C07D 235/04* (2006.01)
*C07D 403/12* (2006.01)

(52) U.S. Cl. ............... 514/397; 548/300.1; 548/302.7; 548/304.7; 548/306.1; 548/316.4; 548/325.1; 514/385; 514/396

(58) Field of Classification Search ............ 548/300.1, 548/301.7, 302.7, 304.7, 308.1, 316.4, 325.1; 514/385, 396, 397
See application file for complete search history.

(56) References Cited

U.S. PATENT DOCUMENTS 6,040,320 A    3/2000   Beers et al.

*Primary Examiner*—Golam M. M. Shameem
(74) *Attorney, Agent, or Firm*—Roxanne Spencer

(57) ABSTRACT

The invention relates to compounds, compositions comprising the compounds, and methods of using the compounds and compound compositions. The compounds, compositions, and methods described herein can be used for the therapeutic modulation of ion channel function, and treatment of disease and disease symptoms, particularly those mediated by certain calcium channel subtype targets.

14 Claims, No Drawings

ION CHANNEL MODULATORS

CROSS-REFERENCE TO RELATED APPLICATIONS

This application claims benefit of U.S. patent application 60/551,371, filed Mar. 8, 2004, the contents of which are incorporated by reference in their entirety.

BACKGROUND

All cells rely on the regulated movement of inorganic ions across cell membranes to perform essential physiological functions. Electrical excitability, synaptic plasticity, and signal transduction are examples of processes in which changes in ion concentration play a critical role. In general, the ion channels that permit these changes are proteinaceous pores consisting of one or multiple subunits, each containing two or more membrane-spanning domains. Most ion channels have selectivity for specific ions, primarily $Na^+$, $K^+$, $Ca^{2+}$, or $Cl^-$, by virtue of physical preferences for size and charge. Electrochemical forces, rather than active transport, drive ions across membranes, thus a single channel may allow the passage of millions of ions per second. Channel opening, or "gating" is tightly controlled by changes in voltage or by ligand binding, depending on the subclass of channel. Ion channels are attractive therapeutic targets due to their involvement in so many physiological processes, yet the generation of drugs with specificity for particular channels in particular tissue types remains a major challenge.

Voltage-gated ion channels open in response to changes in membrane potential. For example, depolarization of excitable cells such as neurons result in a transient influx of $Na^+$ ions, which propagates nerve impulses. This change in $Na^+$ concentration is sensed by voltage-gated $K^+$ channels, which then allow an efflux of $K^+$ ions. The efflux of $K^+$ ions repolarizes the membrane. Other cell types rely on voltage-gated $Ca^{2+}$ channels to generate action potentials. Voltage-gated ion channels also perform important functions in non-excitable cells, such as the regulation of secretory, homeostatic, and mitogenic processes. Ligand-gated ion channels can be opened by extracellular stimuli such as neurotransmitters (e.g., glutamate, serotonin, acetylcholine), or intracellular stimuli (e.g. cAMP, $Ca^{2+}$, and phosphorylation).

The $Ca_v2$ family of voltage-gated calcium channels consists of 3 main subtypes $Ca_v2.1$ (P or Q-type calcium currents), $Ca_v2.2$ (N-type calcium currents) and $Ca_v2.3$ (R-type calcium currents). These currents are found almost exclusively in the central nerves system (CNS), peripheral nerves system (PNS) and neuroendocrine cells and constitute the predominant forms of presynaptic voltage-gated calcium current. Presynaptic calcium entry is modulated by many types of G-protein coupled receptors (GPCRs) and modulation of $Ca_v2$ channels is a widespread and highly efficacious means of regulating neurotransmission. The subunit composition of the $Ca_v2$ channels is defined by their $\alpha_1$ subunit, which forms the pore and contains the voltage-sensing gates ($\alpha_12.1$, $\alpha_12.2$ and $\alpha_12.3$, also known as $\alpha_{1A}$, $\alpha_{1B}$ and $\alpha_{1E}$ respectively) and the $\beta$, $\alpha_2\delta$ and $\gamma$ subunits.

Genetic or pharmacological perturbations in ion channel function can have dramatic clinical consequences. Long QT syndrome, epilepsy, cystic fibrosis, and episodic ataxia are a few examples of heritable diseases resulting from mutations in ion channel subunits. Toxic side affects such as arrhythmia and seizure which are triggered by certain drugs are due to interference with ion channel function (Sirois, J. E. and, Atchison, W. D., *Neurotoxicology* 1996; 17(1):63-84; Keating, M. T., *Science* 1996 272:681-685). Drugs are useful for the therapeutic modulation of ion channel activity, and have applications in treatment of many pathological conditions, including hypertension, angina pectoris, myocardial ischemia, asthma, bladder overactivity, alopecia, pain, heart failure, dysmenorrhea, type II diabetes, arrhythmia, graft rejection, seizure, convulsions, epilepsy, stroke, gastric hypermotility, psychoses, cancer, muscular dystrophy, and narcolepsy (Coghlan, M. J., et al. *J. Med Chem.* 2001, 44:1627-1653; Ackerman. M. J., and Clapham, D. E. *N. Eng. J. Med.* 1997, 336:1575-1586). The growing number of identified ion channels and understanding of their complexity will assist in future efforts at therapies, which modify ion channel function.

Therapeutic modulation of $Ca_v2$ channel activity has applications in treatment of many pathological conditions. All primary sensory afferents provide input to neurons in the dorsal horns of the spinal cord and in dorsal root ganglia neurons in the dorsal horn and calcium influx through $Ca_v2.2$ channels triggers the release of neurotransmitters form presynaptic nerve terminals in the spinal cord. Hence blockade of $Ca_v2.2$ channels is expected to be broadly efficacious because these channels are in a common pathway downstream form the wide variety of receptors that mediate pain (Julius, D. and Basbaum, A. I. *Nature* 2001, 413:203-216). Indeed, intrathecal injection of $Ca_v2.2$ selective conopeptide ziconitide (SNX-111) has been shown to be broadly effective against both neuropathic pain and inflammatory pain in animals and man (Bowersox, S. S. et al, *J Pharmacol Exp Ther* 1996, 279:1243-1249). Ziconotide has also been shown to be highly effective as a neuroprotective agent in rat models of global or focal ischemia (Colburne, F. et al, *Stroke* 1999, 30:662-668). Thus it is reasonable to conclude that modulation of $Ca_v2.2$ has implications in the treatment of neuroprotection/stroke.

$Ca_v2.2$ channels are found in the periphery and mediate catecholamine release from sympathetic neurons and adrenal chroffin cells. Some forms of hypertension result from elevated sympathetic tone and $Ca_v2.2$ modulators could be particularly effective in treating this disorder. Although complete block of $Ca_v2.2$ can cause hypotension or impair baroreceptor reflexes, partial inhibition by $Ca_v2.2$ modulators might reduce hypertension with minimal reflex tachycardia (Uneyama, O. D. *Int. J. Mol. Med.* 1999 3:455-466).

Overactive bladder (OAB) is characterized by storage symptoms such as urgency, frequency and nocturia, with or without urge incontinence, resulting from the overactivity of the detrusor muscle in the bladder. OAB can lead to urge incontinence. The etiology of OAB and painful bladder syndrome is unknown, although disturbances in nerves, smooth muscle and urothelium can cause OAB (Steers, W. *Rev Urol*, 4:S7-S18). There is evidence to suggest that reduction of bladder hyperactivity may be indirectly effected by inhibition of $Ca_v2.2$ and/or $Ca_v1$ channels.

The localization of $Ca_v2.1$ channels in the superficial laminae of the dorsal horn of the spinal cord suggests involvement of these channels in the perception and maintenance of certain forms of pain (Vanegas, H. and Schaible, H. *Pain* 2000, 85:9-18. Complete elimination of $Ca_v2.1$ calcium currents alters synaptic transmission, resulting in severe ataxia. Gabapentin has been used clinically for many years as an add-on therapy for the treatment of epilepsy. In recent years, it has emerged as a leading treatment of neuropathic pain. Clinical trials have shown gabapentin to be effective for the treatment of post-herpetic neuralgia, diabetic neuropathy, trigeminal neuralgia, migrane and fibromyalgia (Mellegers, P. G. et al *Clin J Pain* 2001, 17:284-295). Gabapentin was designed as a metabolically stable GABA mimetic, but most studies find no effect on the GABA receptors. The $\alpha_2\delta$ subunit of the $Ca_v2.1$ channel has been identified as a high affinity binding site for gabapentin in the CNS. There is evidence that suggests that gabapentin could inhibit neurotransmission in the spinal cord by interfering with the function of the $\alpha_2\delta$ subunits thereby inhibiting presynaptic calcium currents.

SUMMARY

The invention relates to heterocyclic compounds, compositions comprising the compounds, and methods of using the compounds and compound compositions. The compounds and compositions comprising them are useful for treating disease or disease symptoms, including those mediated by or associated with ion channels.

In one aspect is a compound of formula (I) or pharmaceutical salt thereof

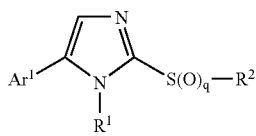

wherein,
Ar$^1$ is cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;
R$^1$ is Ar$^2$ or lower alkyl optionally substituted with Ar$^2$;
Ar$^2$ is independently selected from cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;
q is 0, 1 or 2;
each R$^2$ is independently selected from $(CH_2)_mCO_2R^3$, $(CH_2)_mCOAr^3$, $(CH_2)_mCONR^3R^4$, $(CH_2)_mAr^3$, $(CH_2)_3Ar^3$, $(CH_2)_nNR^3R^4$ or $(CH_2)_nOR^4$;
each R$^3$ is independently selected from H, or lower alkyl;
each R$^4$ is independently selected from H, lower alkyl or $(CH_2)_pAr^3$;
each Ar$^3$ is cycloalkyl, aryl, heterocyclyl, or heteroaryl, each optionally substituted with one or more substituents, with the proviso that Ar$^3$ is not piperidinyl, tetrahydroquinolinyl or tetrahydroisoquinolinyl;
each m is 1 or 2;
each n is 2 or 3;
each p is 0 or 1;
each substituent for Ar$^1$, Ar$^2$ and Ar$^3$ is independently selected from halogen, CN, NO$_2$, OR$^5$, SR$^5$, S(O)$_2$OR$^5$, NR$^5$R$^6$, cycloalkyl, C$_1$-C$_2$ perfluoroalkyl, C$_1$-C$_2$ perfluoroalkoxy, 1,2-methylenedioxy, C(O)OR$^5$, C(O)NR$^5$R$^6$, OC(O)NR$^5$R$^6$, NR$^5$C(O)NR$^5$R$^6$, C(NR$^6$) NR$^5$R$^6$, NR$^5$C(NR$^6$)NR$^5$R$^6$, S(O)$_2$NR$^5$R$^6$, R$^7$, C(O)R$^7$, NR$^5$C(O)R$^7$, S(O)R$^7$, or S(O)$_2$R$^7$;

each R$^5$ is independently selected from hydrogen or lower alkyl optionally substituted with one or more substituents independently selected from halogen, OH, C$_1$-C$_4$ alkoxy, NH$_2$, C$_1$-C$_4$ alkylamino, C$_1$-C$_4$ dialkylamino or C$_3$-C$_6$ cycloalkyl;

each R$^6$ is independently selected from hydrogen, $(CH_2)_p$Ar$^4$, or lower alkyl optionally substituted with one or more substituents independently selected from halogen, OH, C$_1$-C$_4$ alkoxy, NH$_2$, C$_1$-C$_4$ alkylamino, C$_1$-C$_4$ dialkylamino or C$_3$-C$_6$ cycloalkyl;

each R$^7$ is independently selected from $(CH_2)_p$Ar$^4$ or lower alkyl optionally substituted with one or more substituent independently selected from halogen, OH, C$_1$-C$_4$ alkoxy, NH$_2$, C$_1$-C$_4$ alkylamino, C$_1$-C$_4$ dialkylamino or C$_3$-C$_6$ cycloalkyl; and each Ar$^4$ is independently selected from C$_3$-C$_6$ cycloalkyl, aryl or heteroaryl, each optionally substituted with one to three substituents independently selected from halogen, OH, C$_1$-C$_4$ alkoxy, NH$_2$, C$_1$-C$_4$ alkylamino, C$_1$-C$_4$ dialkylamino or 1,2-methylenedioxy.

In other aspects, the compounds are those of any of the formulae herein (including any combinations thereof):

Wherein,
Ar$^1$ is cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;
R$^1$ is Ar$^2$ or lower alkyl optionally substituted with Ar$^2$;
Ar$^2$ is independently selected from cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;
q is 0;
each R$^2$ is independently selected from $(CH_2)_mCO_2R^3$, $(CH_2)_mCOAr^3$, $(CH_2)_mCONR^3R^4$, $(CH_2)_mAr^3$, $(CH_2)_3Ar^3$, $(CH_2)_nNR^3R^4$ or $(CH_2)_nOR^4$;
each R$^3$ is independently selected from H, or lower alkyl;
each R$^4$ is independently selected from H, lower alkyl or $(CH_2)_p$Ar$^3$;
each Ar$^3$ is cycloalkyl, aryl, heterocyclyl, or heteroaryl, each optionally substituted with one or more substituents, with the proviso that Ar$^3$ is not piperidinyl, tetrahydroquinolinyl or tetrahydroisoquinolinyl;
each m is 1 or 2;
each n is 2 or 3;
each p is 0 or 1;
each substituent for Ar$^1$, Ar$^2$ and Ar$^3$ is independently selected from halogen, CN, NO$_2$, OR$^5$, SR$^5$, S(O)$_2$OR$^5$, NR$^5$R$^6$, cycloalkyl, C$_1$-C$_2$ perfluoroalkyl, C$_1$-C$_2$ perfluoroalkoxy 1,2-methylenedioxy, C(O)OR$^5$, C(O) NR$^5$R$^6$, OC(O)NR$^5$R$^6$, NR$^5$C(O)NR$^5$R$^6$, C(NR$^6$) NR$^5$R$^6$, NR$^5$C(NR$^6$)NR$^5$R$^6$, S(O)$_2$NR$^5$R$^6$, R$^7$, C(O)R$^7$, NR$^5$C(O)R$^7$, S(O)R$^7$, or S(O)$_2$R$^7$;
each R$^5$ is independently selected from hydrogen or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^6$ is independently selected from hydrogen, $(CH_2)_p Ar^4$, or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^7$ is independently selected from $(CH_2)_p Ar^4$ or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl; and each $Ar^4$ is independently selected from $C_3$-$C_6$ cycloalkyl, aryl or heteroaryl, each optionally substituted with one to three substituents independently selected from halogen, OH, $C_1$-$C_4$ alkoxy, $NH^2$, $C_1$-$C_4$ alkylamino, $C_1$-$C_4$ dialkylamino or 1,2-methylenedioxy;

Wherein, $Ar^1$ is cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;

$R^1$ is $Ar^2$ or lower alkyl optionally substituted with $Ar^2$;

$Ar^2$ is independently selected from cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;

q is 1;

each $R^2$ is independently selected from $(CH_2)_m CO_2 R^3$, $(CH_2)_m COAr^3$, $(CH_2)_m CONR^3 R^4$, $(CH_2)_m Ar^3$, $(CH_2)_3 Ar^3$, $(CH_2)_n NR^3 R^4$ or $(CH_2)_n OR^4$;

each $R^3$ is independently selected from H, or lower alkyl;

each $R^4$ is independently selected from H, lower alkyl or $(CH_2)_p Ar^3$;

each $Ar^3$ is cycloalkyl, aryl, heterocyclyl, or heteroaryl, each optionally substituted with one or more substituents, with the proviso that $Ar^3$ is not piperidinyl, tetrahydroquinolinyl or tetrahydroisoquinolinyl;

each m is 1 or 2;

each n is 2 or 3;

each p is 0 or 1;

each substituent for $Ar^1$, $Ar^2$ and $Ar^3$ is independently selected from halogen, CN, $NO_2$, $OR^5$, $SR^5$, $S(O)_2 OR^5$, $NR^5 R^6$, cycloalkyl, $C_1$-$C_2$ perfluoroalkyl, $C_1$-$C_2$ perfluoroalkoxy, 1,2-methylenedioxy, $C(O)OR^5$, $C(O)NR^5 R^6$, $OC(O)NR^5 R^6$, $NR^5 C(O)NR^5 R^6$, $C(NR^6)NR^5 R^6$, $NR^5 C(NR^6)NR^5 R^6$, $S(O)_2 NR^5 R^6$, $R^7$, $C(O)R^7$, $NR^5 C(O)R^7$, $S(O)R^7$, or $S(O)_2 R^7$;

each $R^5$ is independently selected from hydrogen or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^6$ is independently selected from hydrogen, $(CH_2)_p Ar^4$, or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^7$ is independently selected from $(CH_2)_p Ar^4$ or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl; and each $Ar^4$ is independently selected from $C_3$-$C_6$ cycloalkyl, aryl or heteroaryl, each optionally substituted with one to three substituents independently selected from halogen, OH, $C_1$-$C_4$ alkoxy, $NH_2$, $C_1$-$C_4$ alkylamino, $C_1$-$C_4$ dialkylamino or 1,2-methylenedioxy;

Wherein, $Ar^1$ is cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;

$R^1$ is $Ar^2$ or lower alkyl optionally substituted with $Ar^2$;

$Ar^2$ is independently selected from cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;

q is 2;

each $R^2$ is independently selected from $(CH_2)_m CO_2 R^3$, $(CH_2)_m COAr^3$, $(CH_2)_m CONR^3 R^4$, $(CH_2)_m Ar^3$, $(CH_2)_3 Ar^3$, $(CH_2)_n NR^3 R^4$ or $(CH_2)_n OR^4$;

each $R^3$ is independently selected from H, or lower alkyl;

each $R^4$ is independently selected from H, lower alkyl or $(CH_2)_p Ar^3$;

each $Ar^3$ is cycloalkyl, aryl, heterocyclyl, or heteroaryl, each optionally substituted with one or more substituents, with the proviso that $Ar^3$ is not piperidinyl, tetrahydroquinolinyl or tetrahydroisoquinolinyl;

each m is 1 or 2;

each n is 2 or 3;

each p is 0 or 1;

each substituent for $Ar^1$, $Ar^2$ and $Ar^3$ is independently selected from halogen, CN, $NO_2$, $OR^5$, $SR^5$, $S(O)_2 OR^5$, $NR^5 R^6$, cycloalkyl, $C_1$-$C_2$ perfluoroalkyl, $C_1$-$C_2$ perfluoroalkoxy, 1,2-methylenedioxy, $C(O)OR^5$, $C(O)NR^5 R^6$, $OC(O)NR^5 R^6$, $NR^5 C(O)NR^5 R^6$, $C(NR^6)NR^5 R^6$, $NR^5 C(NR^6)NR^5 R^6$, $S(O)_2 NR^5 R^6$, $R^7$, $C(O)R^7$, $NR^5 C(O)R^7$, $S(O)R^7$, or $S(O)_2 R^7$;

each $R^5$ is independently selected from hydrogen or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^6$ is independently selected from hydrogen, $(CH_2)_p Ar^4$, or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^7$ is independently selected from $(CH_2)_p Ar^4$ or lower alkyl optionally substituted with one or more substituents independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl; and each $Ar^4$ is independently selected from $C_3$-$C_6$ cycloalkyl, aryl or heteroaryl, each optionally substituted with one to three substituents independently selected from halogen, OH, $C_1$-$C_4$ alkoxy, $NH_2$, $C_1$-$C_4$ alkylamino, $C_1$-$C_4$ dialkylamino or 1,2-methylenedioxy;

Wherein,
$R^2$ is $(CH_2)_mCO_2R^3$, $(CH_2)_mCOAr^3$, or $(CH_2)_mCONR^3R^4$, and m is 2;

Wherein,
$R^1$ is $Ar^2$ or lower alkyl substituted with $Ar^2$, $R^2$ is $(CH_2)_mAr^3$, and m is 1, with the proviso that $R^1$ is not furylmethyl or tetrahydrofurylmethyl;

Wherein,
$R^1$ is $Ar^2$ or lower alkyl substituted with $Ar_2$, $R^2$ is $(CH_2)_mAr^3$, and m is 2, with the proviso that $R^1$ is not furylmethyl or tetrahydrofurylmethyl;

Wherein,
$Ar^1$ and $R^1$ are each an optionally substituted aryl, and $R^2$ is independently selected from $(CH_2)_mAr^3$, $(CH_2)_3Ar^3$, $(CH_2)_nNR^3R^4$ or $(CH_2)_nOR^4$;

Wherein,
each $R^2$ is independently selected from $(CH_2)_mAr^3$, and each $Ar^3$ is heteroaryl optionally substituted with one or more substituents;

Wherein,
$Ar^3$ is heteroaryl having a five-membered ring of carbon atoms and 1, 2 or 3 heteroatoms selected from N, O and S, optionally substituted with one or more substituents;

Wherein,
$Ar^3$ is pyrrolidinyl, pyrazolyl, imidazolyl, thioimidazolyl, benzimidazolyl, or benzthioimidazolyl, each optionally substituted with one or more substituents;

Wherein, the compound of formula I is a compound delineated in any of the tables herein or pharmaceutical salt thereof.

In other aspects, the invention relates to a composition comprising a compound of any of the formulae herein, an additional therapeutic agent, and a pharmaceutically acceptable carrier. The additional therapeutic agent can be a cardiovascular disease agent and/or a nervous system disease agent. A nervous system disease agent refers to a peripheral nervous system (PNS) disease agent and/or a central nervous system (CNS) disease agent.

Yet another aspect of this invention relates to a method of treating a subject (e.g., mammal, human, horse, dog, cat) having a disease or disease symptom (including, but not limited to angina, hypertension, congestive heart failure, myocardial ischemia, arrhythmia, diabetes, urinary incontinence, stroke, pain, traumatic brain injury, or a neuronal disorder). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Yet another aspect of this invention relates to a method of treating a subject (e.g., mammal, human, horse, dog, cat) having an ion channel mediated disease or disease symptom (including, but not limited to angina, hypertension, congestive heart failure, myocardial ischemia, arrhythmia, diabetes, urinary incontinence, stroke, pain, traumatic brain injury, or a neuronal disorder). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Another aspect is a method of modulating (e.g., inhibiting, agonism, antagonism) calcium channel activity comprising contacting a calcium channel with a compound (or composition thereof) of any of the formulae herein.

Other aspects are a method of modulating calcium channel $Ca_v2$ activity in a subject in need thereof including administering to the subject a therapeutically effective amount of a compound (or composition thereof) of any of the formulae herein.

The invention also relates to a method of making a compound described herein, the method including any reactions or reagents as delineated in the schemes or examples herein. Alternatively, the method includes taking any one of the intermediate compounds described herein and reacting it with one or chemical reagents in one or more steps to produce a compound described herein.

Also within the scope of this invention is a packaged product. The packaged product includes a container, one of the aforementioned compounds in the container, and a legend (e.g., a label or an insert) associated with the container and indicating administration of the compound for treating a disorder associated with ion channel modulation.

In other embodiments, the compounds, compositions, and methods delineated herein are any of the compounds of Table 1 herein or methods including them.

The details of one or more embodiments of the invention are set forth in the accompanying drawings and the description below. Other features, objects, and advantages of the invention will be apparent from the description and from the claims.

DETAILED DESCRIPTION

As used herein, the term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_5$ indicates that the group may have from 1 to 5 (inclusive) carbon atoms in it. The term "lower alkyl" refers to a $C_1$-$C_6$ alkyl chain. The term "arylalkyl" refers to a moiety in which an alkyl hydrogen atom is replaced by an aryl group.

The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene.

The term "cycloalkyl" as employed herein includes saturated and partially unsaturated cyclic hydrocarbon groups having 3 to 12 carbons, preferably 3 to 8 carbons, and more preferably 3 to 6 carbon.

The term "aryl" refers to a 6-membered monocyclic or 10- to 14-membered multicyclic aromatic hydrocarbon ring system wherein 0, 1, 2, 3, or 4 atoms of each ring may be substituted by a substituent. Examples of aryl groups include phenyl, naphthyl and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, aryl, heterocyclyl, or heteroaryl group at any atom of that group. Suitable substituents include, without limitation halogen, CN, $NO_2$, $OR^5$, $SR^5$, $S(O)_2OR^5$, $NR^5R^6$, $C_1$-$C_2$ perfluoroalkyl, $C_1$-$C_2$ perfluoroalkoxy, 1,2-methylenedioxy, $C(O)OR^5$, $C(O)NR^5R^6$, $OC(O)NR^5R^6$, $NR^5C(O)NR^5R^6$, $C(NR^6)NR^5R^6$, $NR^5C(NR^6)NR^5R^6$, $S(O)_2 NR^5R^6$, $R^7$, $C(O)R^7$, $NR^5C(O)R^7$, or $S(O)_2R^7$. Each $R^5$ is independently hydrogen, $C_1$-$C_4$ alkyl or $C_3$-$C_6$ cycloalkyl. Each $R^6$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^7$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^5$, $R^6$ and $R^7$ can optionally be substituted with halogen, CN, $C_1$-$C_4$ alkyl, OH, $C_1$-$C_4$ alkoxy, $NH_2$, $C_1$-$C_4$ alkylamino, $C_1$-$C_4$ dialkylamino, $C_1$-$C_2$ perfluoroalkyl, $C_1$-$C_2$ perfluoroalkoxy, or 1,2-methylenedioxy.

In one aspect, the substituents on a group are independently, hydrogen, hydroxyl, halogen, nitro, $SO_3H$, trifluoromethyl, trifluoromethoxy, alkyl (C1-C6 straight or branched), alkoxy (C1-C6 straight or branched), O-benzyl, O-phenyl, phenyl, 1,2-methylenedioxy, carboxyl, morpholinyl, piperidinyl, amino or $OC(O)NR^5R^6$. Each $R^5$ and $R^6$ is as described above.

The term "treating" or "treated" refers to administering a compound described herein to a subject with the purpose to cure, heal, alleviate, relieve, alter, remedy, ameliorate, improve, or affect a disease, the symptoms of the disease or the predisposition toward the disease.

"An effective amount" refers to an amount of a compound, which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg. Effective doses will also vary depending on route of administration, as well as the possibility of co-usage with other agents.

Representative compounds useful in the compositions and methods are delineated herein:

TABLE 1A

| Cpd No. | $Ar^1$ | $R^1$ | $R^2$ |
|---|---|---|---|
| 1 | 4-F-phenyl | 4-Cl-phenyl | 2-ethylbenzimidazole |
| 2 | phenyl | 4-CH₃-phenyl | 2-ethylbenzimidazole |
| 3 | 2-CH₃-phenyl | 4-CH₃-phenyl | 2-ethylbenzimidazole |
| 4 | 4-F-phenyl | 4-CH₃-phenyl | 2-ethylbenzimidazole |

TABLE 1A-continued
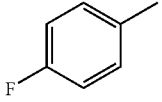
| Cpd No. | Ar¹ | R¹ | R² |
|---|---|---|---|
| 5 | 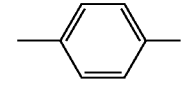 | 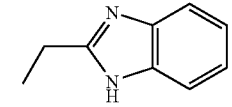 | 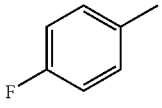 |
| 6 | 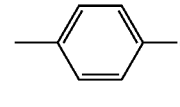 | 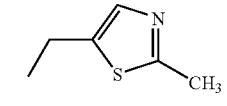 | 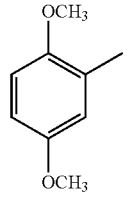 |
| 7 | 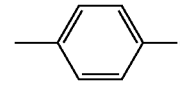 | 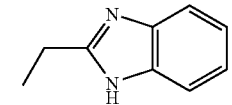 | 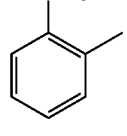 |
| 8 | 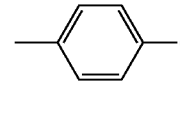 | 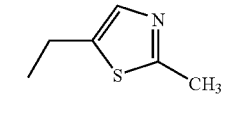 | 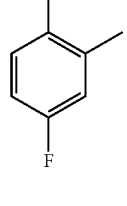 |
| 9 | 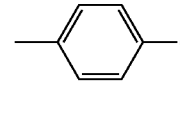 | 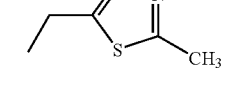 | 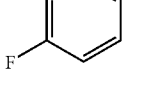 |
| 10 | 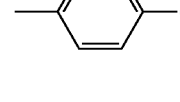 | 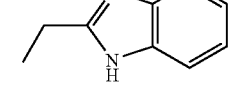 | 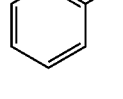  Sulfur is oxicized to Sulfoxide |
| 11 | 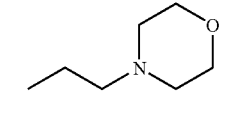 | Et | 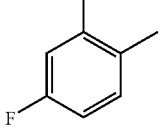 |
| 12 | 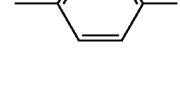 | 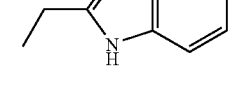 | (see above) |

TABLE 1A-continued
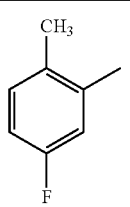
| Cpd No. | Ar¹ | R¹ | R² |
|---|---|---|---|
| 13 | 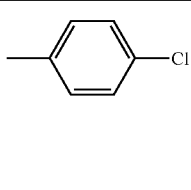 | 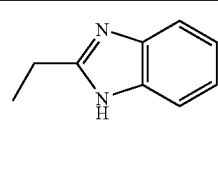 | 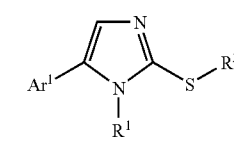 |
| 14 | 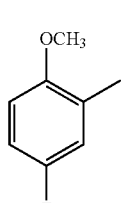 | 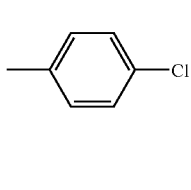 | 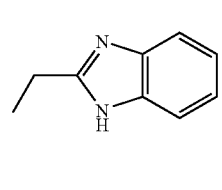 |
| 15 | 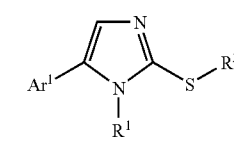 | 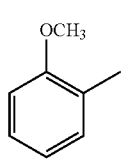 | 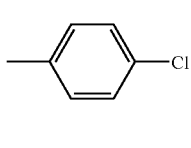 |
| 16 | 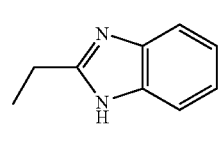 | 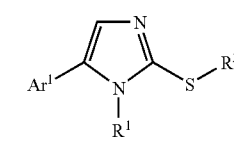 | 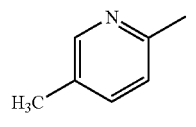 |
| 17 | 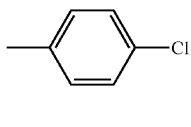 | 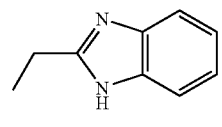 | 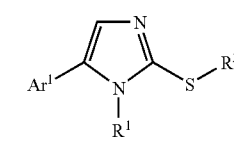 |
| 18 | 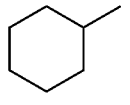 | 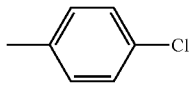 | 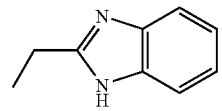 |
| 19 | 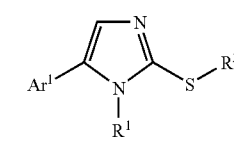 | 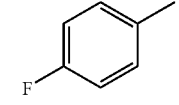 | 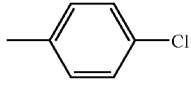 |
| 20 | 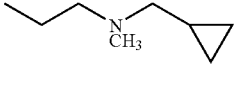 | 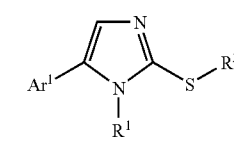 | 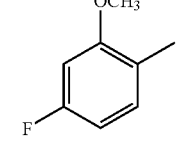 |

TABLE 1A-continued
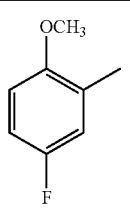
| Cpd No. | Ar¹ | R¹ | R² |
|---|---|---|---|
| 21 | 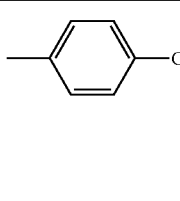 | 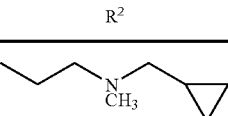 | 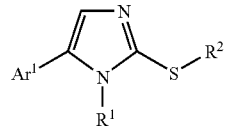 |
| 22 | 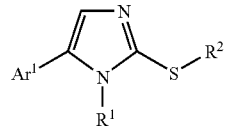 | 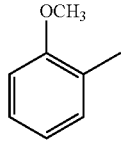 | 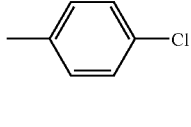 |
| 23 | 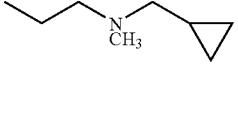 | 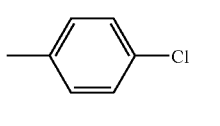 | 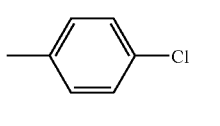 |
| 24 | 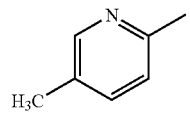 | 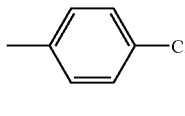 | 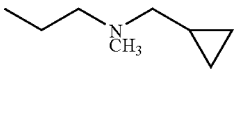 |
| 25 | 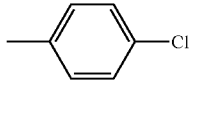 | 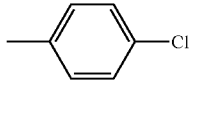 | 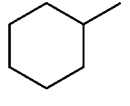 |
| 26 | 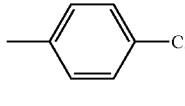 | 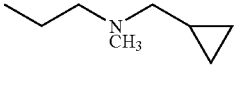 | 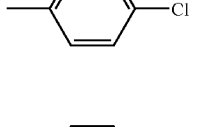 |
| 27 | 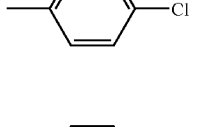 | 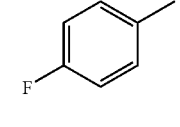 | 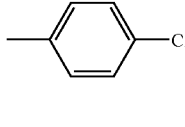 |
| 28 | 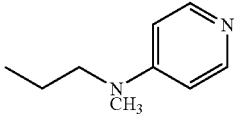 | 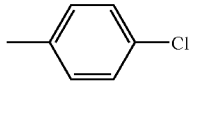 | 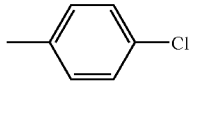 |

TABLE 1A-continued
| Cpd No. | Ar¹ | R¹ | R² |
|---|---|---|---|
| 29 | 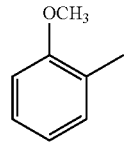 | 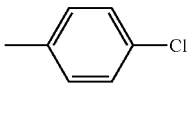 | 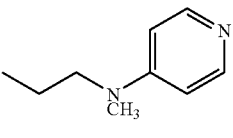 |
| 30 | 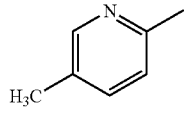 | 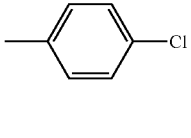 | 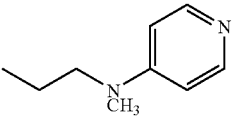 |
| 31 | 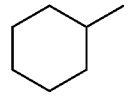 | 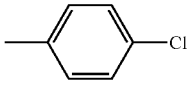 | 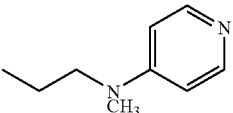 |
| 32 | 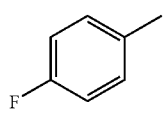 | 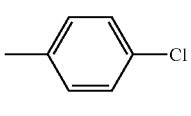 | 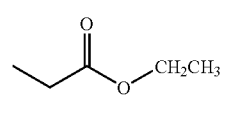 |
| 33 | 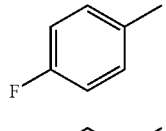 | 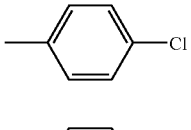 | 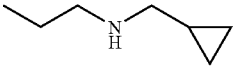 |
| 34 | 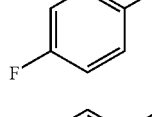 | 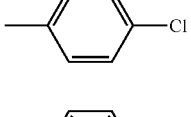 | 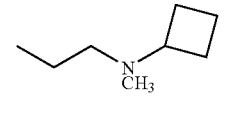 |
| 35 | 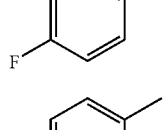 | 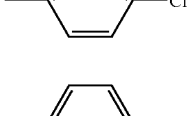 | 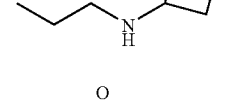 |
| 36 | 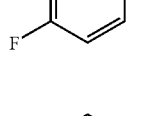 | 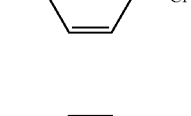 | 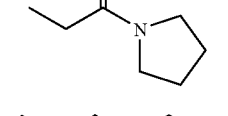 |
| 37 | 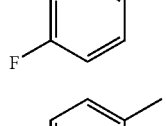 | 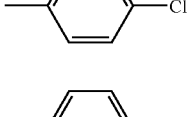 | 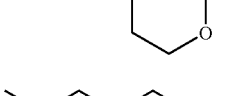 |
| 38 | 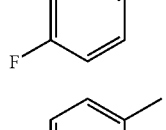 | 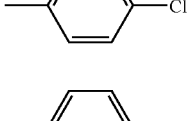 | 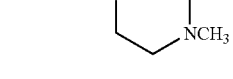 |
| 39 | 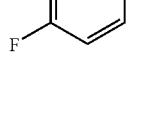 | 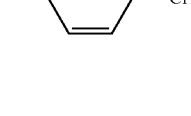 | 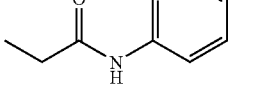 |

TABLE 1A-continued
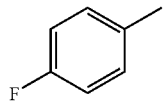
| Cpd No. | Ar¹ | R¹ | R² |
|---|---|---|---|
| 40 | 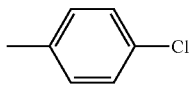 | 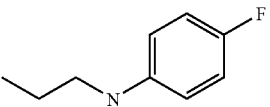 | 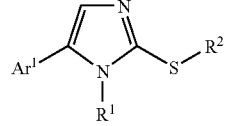 |
| 41 |  | 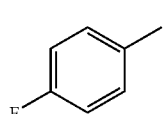 | 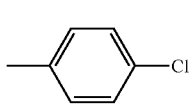 |
| 42 | 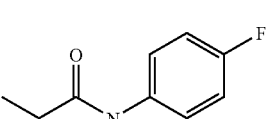 | 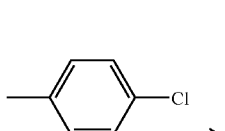 | 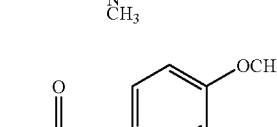 |
| 43 | 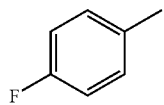 | 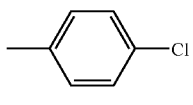 | 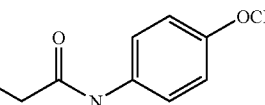 |
| 44 | 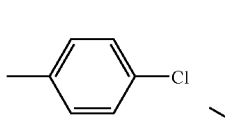 | 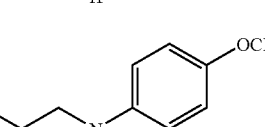 | 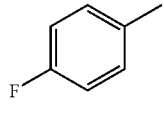 |
| 45 | 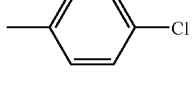 | 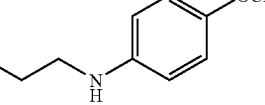 | 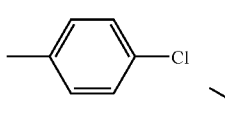 |
| 46 | 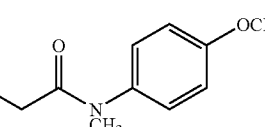 | 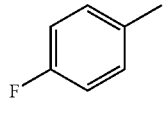 | 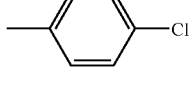 |
| 47 | 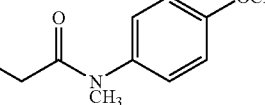 | 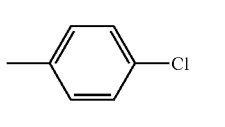 | 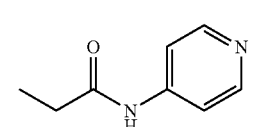 |
| 48 | 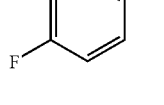 | 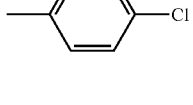 | 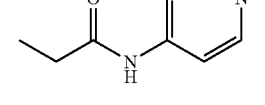 |
| 49 | 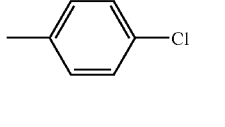 | 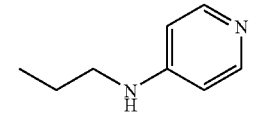 | 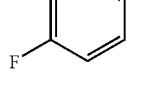 |

TABLE 1A-continued
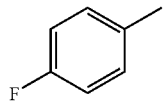
| Cpd No. | Ar¹ | R¹ | R² |
|---|---|---|---|
| 50 | 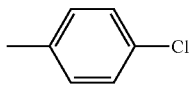 | 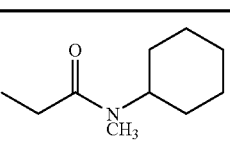 | 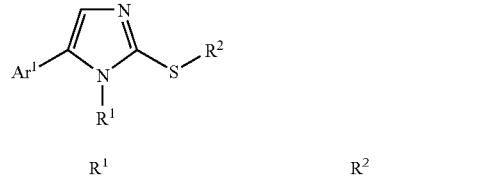 |
| 51 | 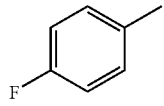 | 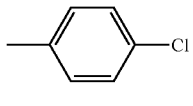 | 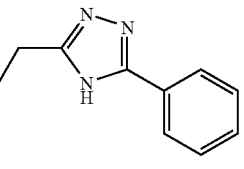 |
| 52 | 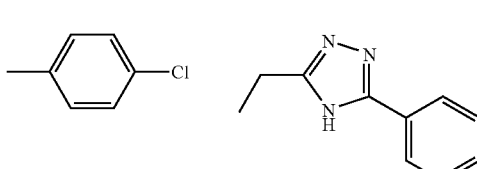 | 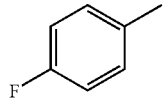 | 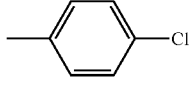 |
| 53 | 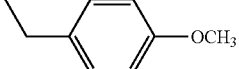 | 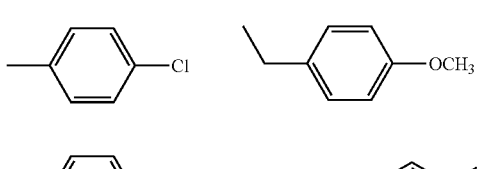 | 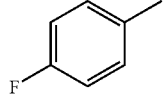 |
| 54 | 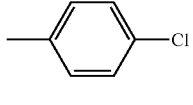 | 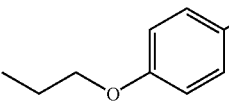 | 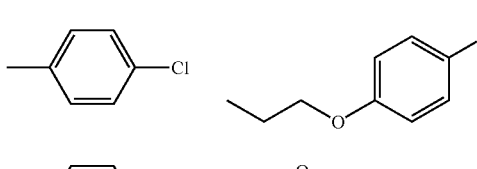 |
| 55 | 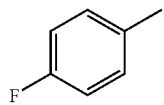 | 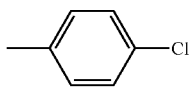 | 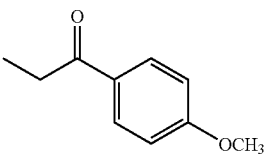 |
| 56 | 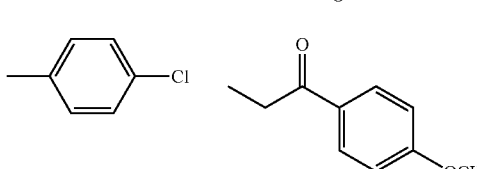 | 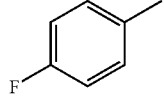 | 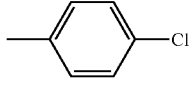 |
| 57 | 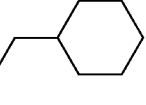 | 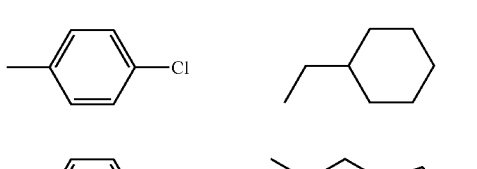 | 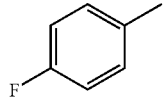 |
| 58 | 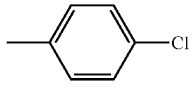 | 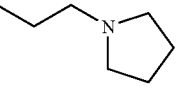 | 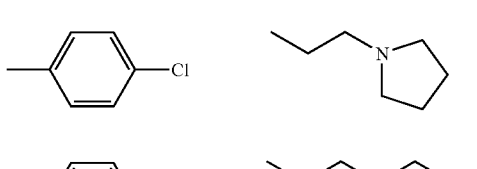 |
| 59 | 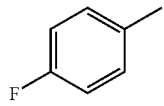 | 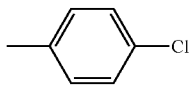 | 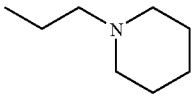 |

TABLE 1A-continued
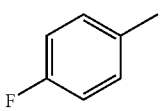
| Cpd No. | Ar¹ | R¹ | R² |
|---|---|---|---|
| 60 | 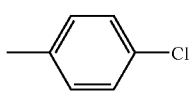 | 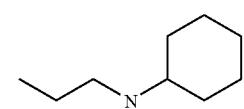 | 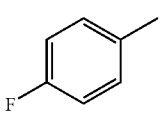 |
| 61 | 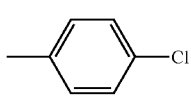 | 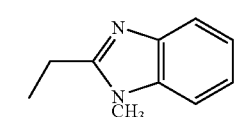 | 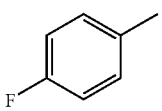 |
| 62 | 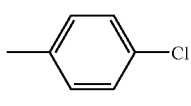 | 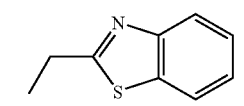 | 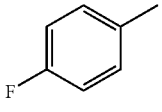 |
| 63 | 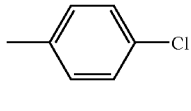 | 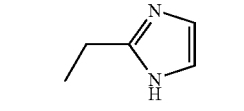 | 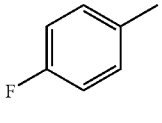 |
| 64 | 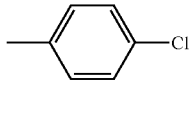 | 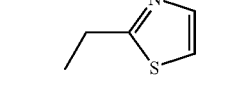 | 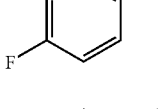 |
| 65 | 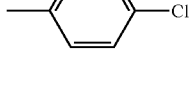 | 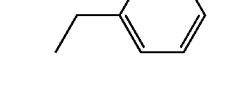 | 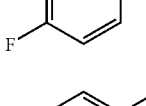 |
| 66 | 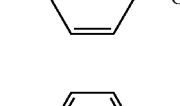 | 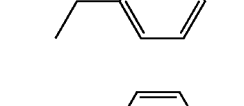 | 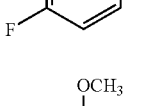 |
| 67 | 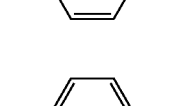 | 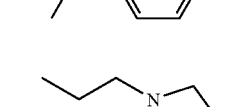 | 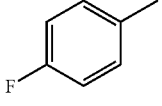 |
| 68 | 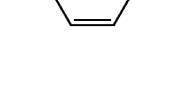 | 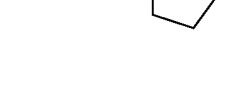 | 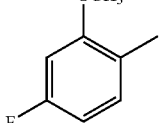 |
| 69 | 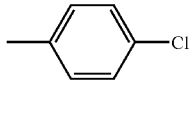 | 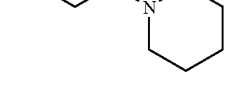 | |

TABLE 1A-continued

| Cpd No. | Ar¹ | R¹ | R² |
| --- | --- | --- | --- |
| 70 | 2-OCH₃, 4-F phenyl | 4-Cl phenyl | N-methyl-N-(4-fluorophenyl)propyl |
| 71 | 2-OCH₃, 4-F phenyl | 4-Cl phenyl | N-methyl-N-(4-methoxyphenyl)propyl |
| 72 | 2-OCH₃, 4-F phenyl | 4-Cl phenyl | N-methyl-N-cyclohexylpropyl |
| 73 | 2-OCH₃, 4-F phenyl | 4-Cl phenyl | 2-ethyl-1-methylbenzimidazole |
| 74 | 2-OCH₃, 4-F phenyl | 4-Cl phenyl | 2-ethylbenzothiazole |
| 75 | 2-OCH₃, 4-F phenyl | 4-Cl phenyl | 2-ethyl-1H-imidazole |
| 76 | 2-OCH₃, 4-F phenyl | 4-Cl phenyl | 2-ethylthiazole |
| 77 | 2-OCH₃, 4-F phenyl | 4-Cl phenyl | 5-ethyl-2-methylthiazole |

TABLE 1A-continued

| Cpd No. | Ar¹ | R¹ | R² |
|---|---|---|---|
| 78 | 2-OCH₃, 4-F, 1-methylphenyl | 4-Cl-phenyl | 2-(pyridin-2-yl)ethyl |
| 79 | 2-OCH₃, 4-F, 1-methylphenyl | 4-Cl-phenyl | 2-(pyridin-3-yl)ethyl |
| 80 | 2-OCH₃, 4-F, 1-methylphenyl | 4-Cl-phenyl | 2-(pyridin-4-yl)ethyl |
| 81 | 2-CH₃, 4-F-phenyl | 4-Cl-phenyl | 3-(pyrrolidin-1-yl)propyl |
| 82 | 2-CH₃, 4-F-phenyl | 4-Cl-phenyl | 3-(piperidin-1-yl)propyl |
| 83 | 2-CH₃, 4-F-phenyl | 4-Cl-phenyl | 3-[N-methyl-N-(4-fluorophenyl)amino]propyl |
| 84 | 2-CH₃, 4-F-phenyl | 4-Cl-phenyl | 3-[N-methyl-N-(4-methoxyphenyl)amino]propyl |

TABLE 1A-continued
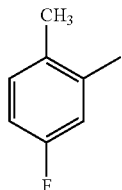
| Cpd No. | Ar¹ | R¹ | R² |
|---|---|---|---|
| 85 | 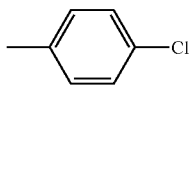 | 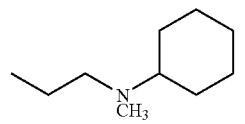 | 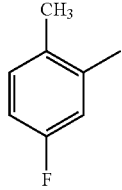 |
| 86 | 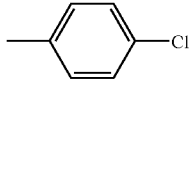 | 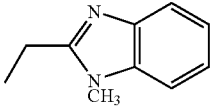 | 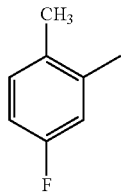 |
| 87 | 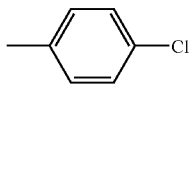 | 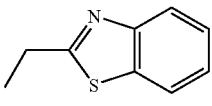 | 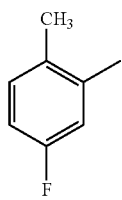 |
| 88 | 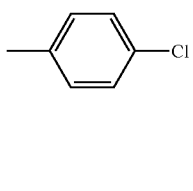 | 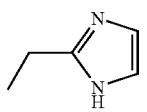 | 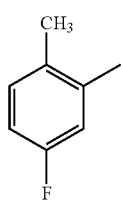 |
| 89 | 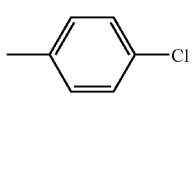 | 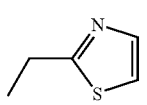 | 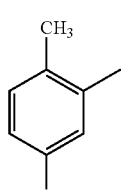 |
| 90 | 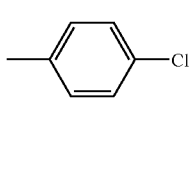 | 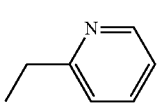 | 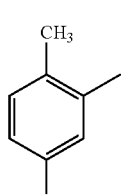 |
| 91 | 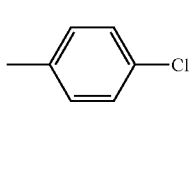 | 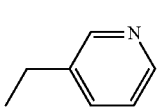 | |

TABLE 1A-continued
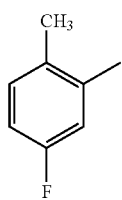
| Cpd No. | Ar¹ | R¹ | R² |
|---|---|---|---|
| 92 | 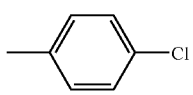 | 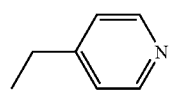 | 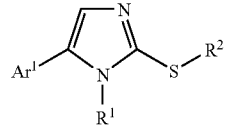 |
| 93 | 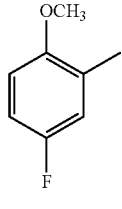 | 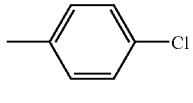 | 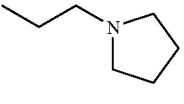 |
| 94 | 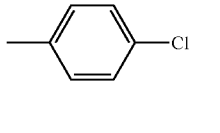 | 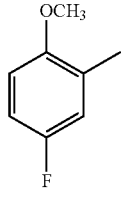 | 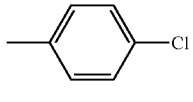 |
| 95 | 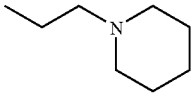 | 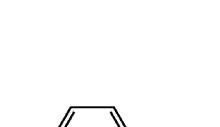 | 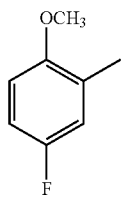 |
| 96 | 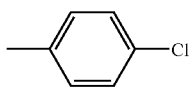 | 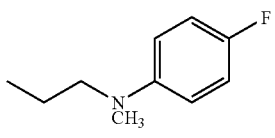 | 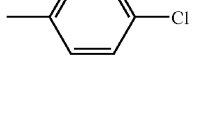 |
| 97 | 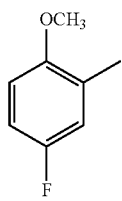 | 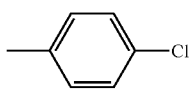 | 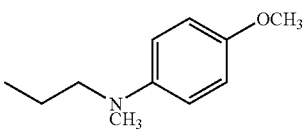 |

TABLE 1A-continued
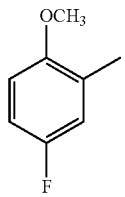
| Cpd No. | Ar¹ | R¹ | R² |
|---|---|---|---|
| 98 | 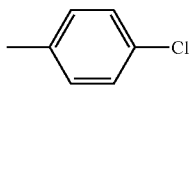 | 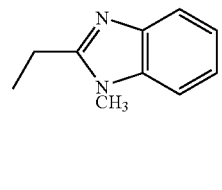 | 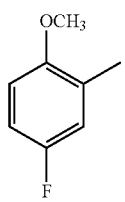 |
| 99 | 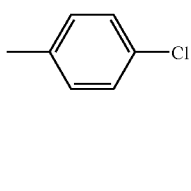 | 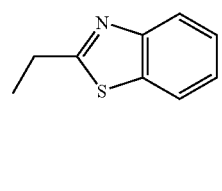 | 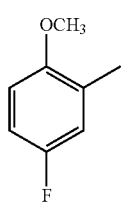 |
| 100 | 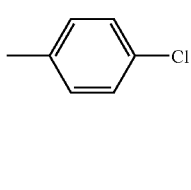 | 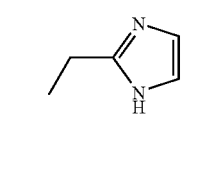 | 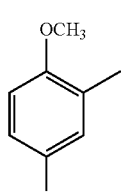 |
| 101 | 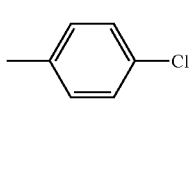 | 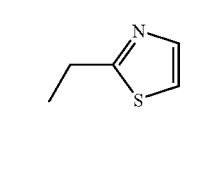 | 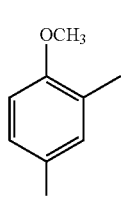 |
| 102 | 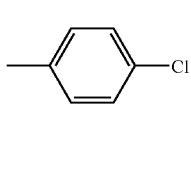 | 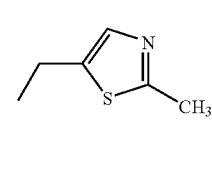 | 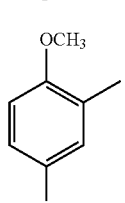 |
| 103 | 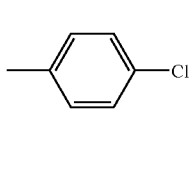 | 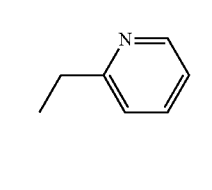 | 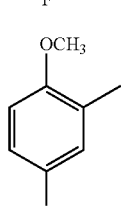 |
| 104 | 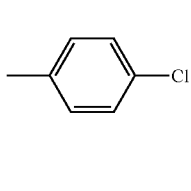 | | 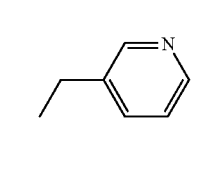 |

TABLE 1A-continued structure: Ar¹-imidazole(N)-S-R² with R¹ on N

| Cpd No. | Ar¹ | R¹ | R² |
|---|---|---|---|
| 105 | 2-methyl-4-fluoro-phenyl with OCH₃ | 4-chlorophenyl | 4-pyridyl-methyl |
| 106 | 4-fluorophenyl | 6-methylpyridin-3-yl | 2-ethyl-1H-benzimidazol-yl |
| 107 | 4-fluorophenyl | CH₃ | 2-ethyl-1H-benzimidazol-yl |
| 108 | 4-fluorophenyl | cyclohexyl | 2-ethyl-1H-benzimidazol-yl |
| 109 | 4-fluorophenyl | 4-chlorobenzyl | 2-ethyl-1H-benzimidazol-yl |
| 110 | 4-fluorophenyl | 4-chlorophenyl | N-methyl-N-(pyridin-4-yl)propyl |
| 111 | 4-fluorophenyl | 4-methylphenyl | N-methyl-N-(pyridin-4-yl)propyl |
| 112 | 4-fluorophenyl | 6-methylpyridin-3-yl | N-methyl-N-(pyridin-4-yl)propyl |
| 113 | 4-fluorophenyl | CH₃ | N-methyl-N-(pyridin-4-yl)propyl |
| 114 | 4-fluorophenyl | cyclohexyl | N-methyl-N-(pyridin-4-yl)propyl |

TABLE 1A-continued
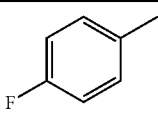
| Cpd No. | Ar¹ | R¹ | R² |
|---|---|---|---|
| 115 | 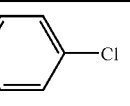 | 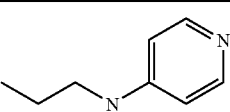 | 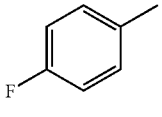 |
| 116 | 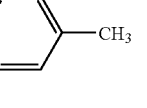 | 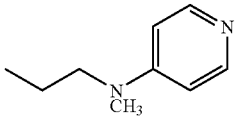 | 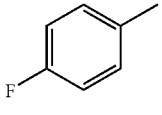 |
| 117 | 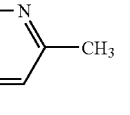 | 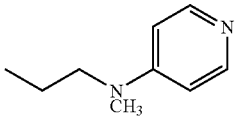 | 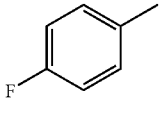 |
| 118 | 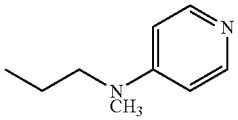 | CH₃ | 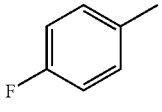 |
| 119 | 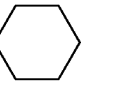 | 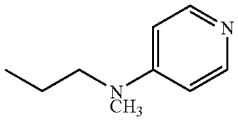 | 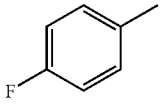 |
| 120 | 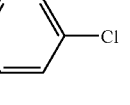 | 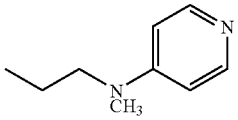 | 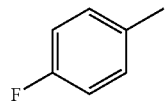 |
TABLE 1B
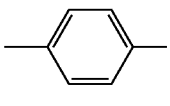
| Cpd No. | Ar¹ | R¹ | R² |
|---|---|---|---|
| 121 | 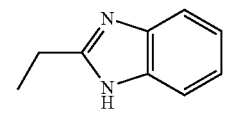 | 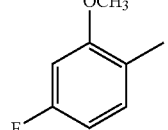 | 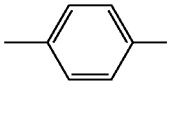 |
| 122 | 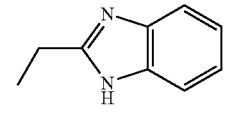 | | |

TABLE 1B-continued

| Cpd No. | Ar¹ | R¹ | R² |
|---|---|---|---|
| 123 | 2-methyl-4-fluoro-phenyl (CH₃ ortho, F para) | 4-chlorophenyl | 2-ethyl-1H-benzimidazol-yl |
| 124 | 2-methoxy-4-fluoro-phenyl | 4-chlorophenyl | 2-ethyl-1H-benzimidazol-yl |
| 125 | 2-methoxyphenyl | 4-chlorophenyl | 2-ethyl-1H-benzimidazol-yl |
| 126 | 2-methyl-5-methyl-pyridinyl | 4-chlorophenyl | 2-ethyl-1H-benzimidazol-yl |
| 127 | cyclohexyl | 4-chlorophenyl | 2-ethyl-1H-benzimidazol-yl |
| 128 | 4-fluorophenyl | 5-chloropyridin-2-yl | N-methyl-N-propyl-cyclopropylmethyl-amine |
| 129 | 2-methoxy-4-fluoro-phenyl | 4-chlorophenyl | N-methyl-N-propyl-cyclopropylmethyl-amine |
| 130 | 2-methyl-4-fluoro-phenyl | 4-chlorophenyl | N-methyl-N-propyl-cyclopropylmethyl-amine |

TABLE 1B-continued
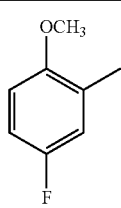
| Cpd No. | Ar¹ | R¹ | R² |
|---|---|---|---|
| 131 | 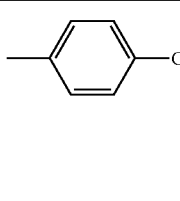 | 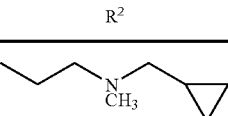 | 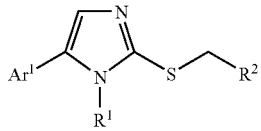 |
| 132 | 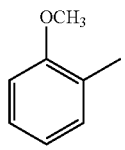 | 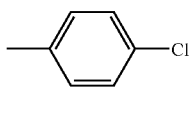 | 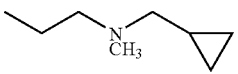 |
| 133 | 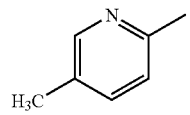 | 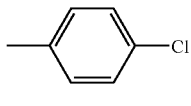 | 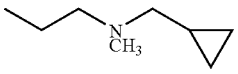 |
| 134 | 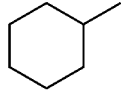 | 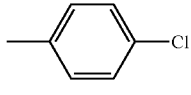 | 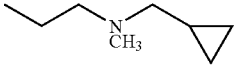 |
| 135 | 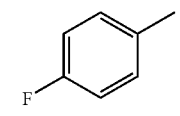 | 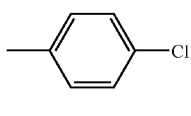 | 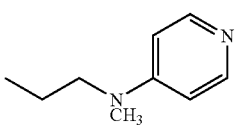 |
| 136 | 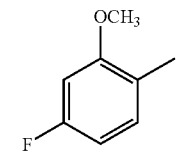 | 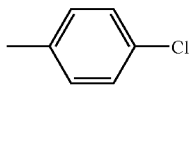 | 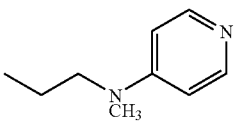 |
| 137 | 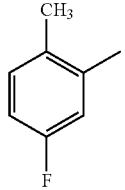 | 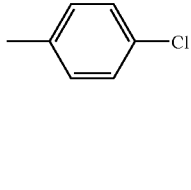 | 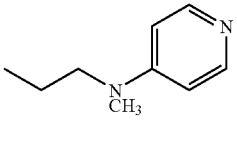 |
| 138 | 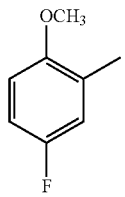 | 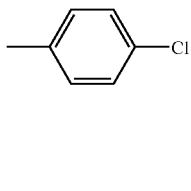 | 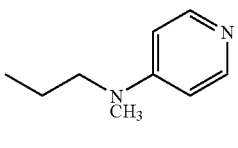 |

TABLE 1B-continued
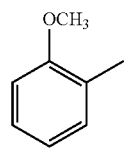
| Cpd No. | Ar¹ | R¹ | R² |
|---|---|---|---|
| 139 | 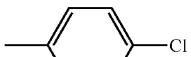 | 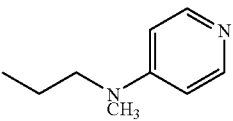 | 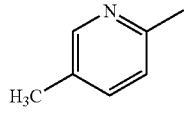 |
| 140 | 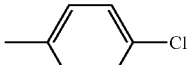 | 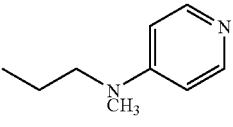 | 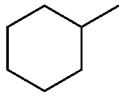 |
| 141 | 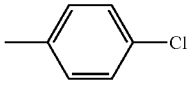 | 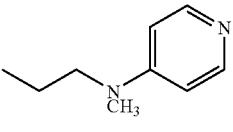 | 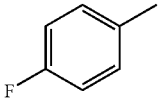 |
| 142 | 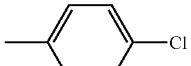 | 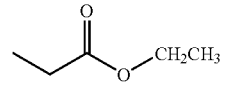 | 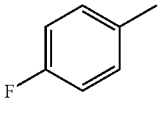 |
| 143 | 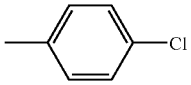 |  | 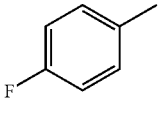 |
| 144 | 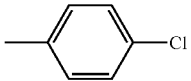 | 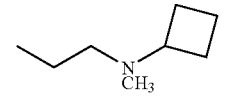 | 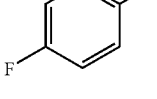 |
| 145 | 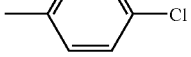 | 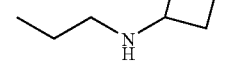 | 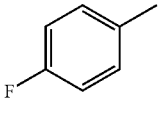 |
| 146 | 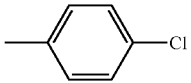 | 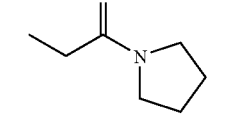 | 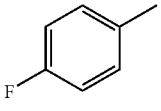 |
| 147 |  | 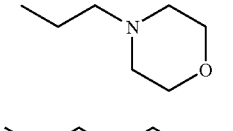 | 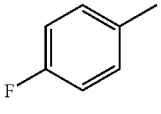 |
| 148 | 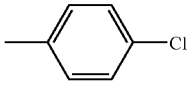 | 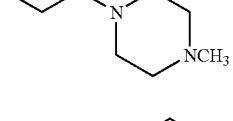 | 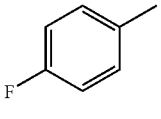 |
| 149 | 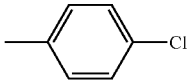 | 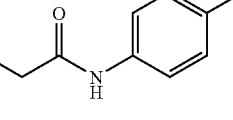 | |

TABLE 1B-continued

| Cpd No. | Ar¹ | R¹ | R² |
|---|---|---|---|
| 150 | 4-F-C6H4 | 4-Cl-C6H4 | -CH2CH2CH2-NH-(4-F-C6H4) |
| 151 | 4-F-C6H4 | 4-Cl-C6H4 | -CH2C(O)-N(CH3)-(4-F-C6H4) |
| 152 | 4-F-C6H4 | 4-Cl-C6H4 | -CH2C(O)-NH-(4-OCH3-C6H4) |
| 153 | 4-F-C6H4 | 4-Cl-C6H4 | -CH2CH2CH2-NH-(4-OCH3-C6H4) |
| 154 | 4-F-C6H4 | 4-Cl-C6H4 | -CH2C(O)-N(CH3)-(4-OCH3-C6H4) |
| 155 | 4-F-C6H4 | 4-Cl-C6H4 | -CH2C(O)-NH-(4-pyridyl) |
| 156 | 4-F-C6H4 | 4-Cl-C6H4 | -CH2CH2CH2-NH-(4-pyridyl) |
| 157 | 4-F-C6H4 | 4-Cl-C6H4 | -CH2C(O)-N(CH3)-(4-pyridyl) |
| 158 | 4-F-C6H4 | 4-Cl-C6H4 | -CH2C(O)-NH-cyclohexyl |
| 159 | 4-F-C6H4 | 4-Cl-C6H4 | -CH2CH2CH2-NH-cyclohexyl |

TABLE 1B-continued
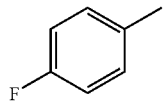
| Cpd No. | Ar¹ | R¹ | R² |
|---|---|---|---|
| 160 | 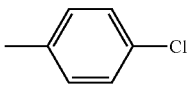 | 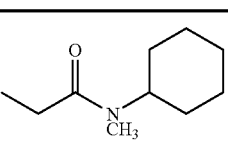 | 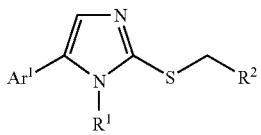 |
| 161 | 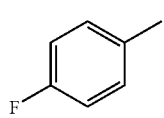 | 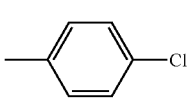 | 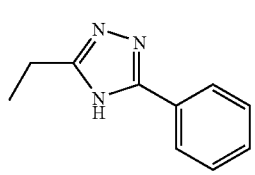 |
| 162 | 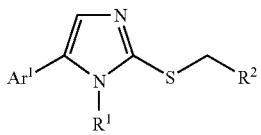 | 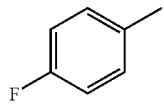 | 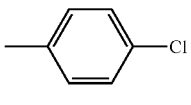 |
| 163 |  | 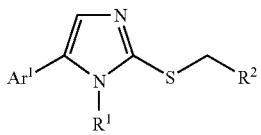 | 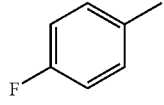 |
| 164 | 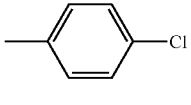 | 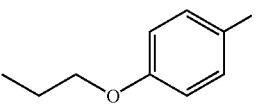 | 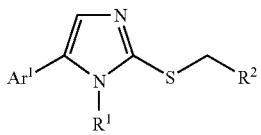 |
| 165 | 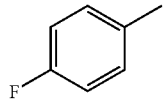 | 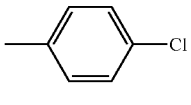 | 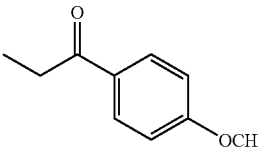 |
| 166 | 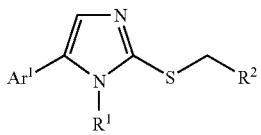 | 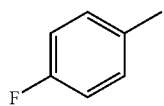 | 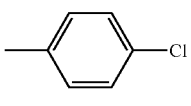 |
| 167 | 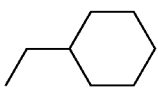 | 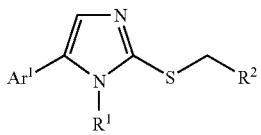 | 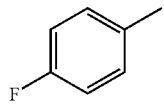 |
| 168 | 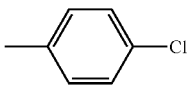 | 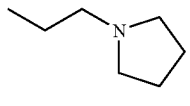 | 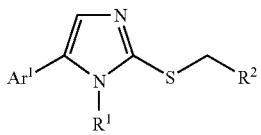 |
| 169 | 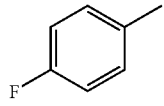 | 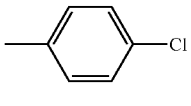 | 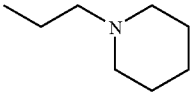 |

TABLE 1B-continued
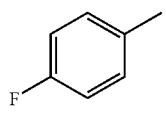
| Cpd No. | Ar¹ | R¹ | R² |
|---|---|---|---|
| 170 | 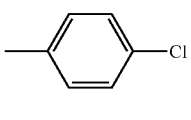 | 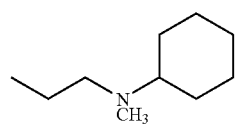 | 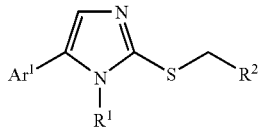 |
| 171 | 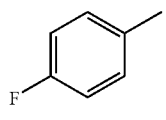 | 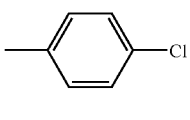 | 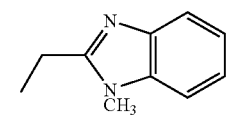 |
| 172 | 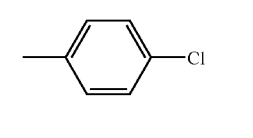 | 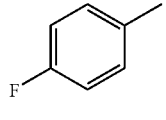 | 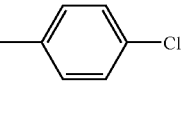 |
| 173 | 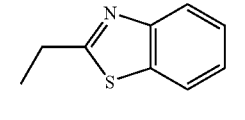 | 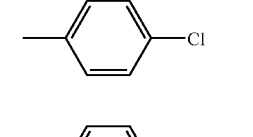 | 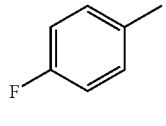 |
| 174 | 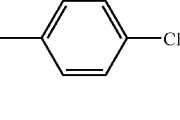 | 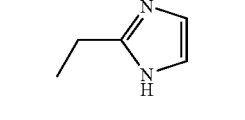 | 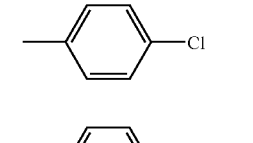 |
| 175 | 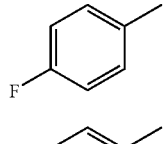 | 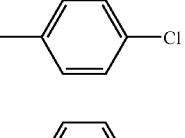 | 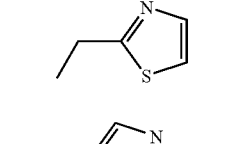 |
| 176 | 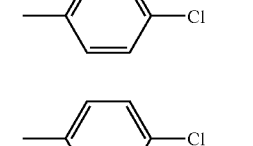 | 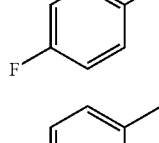 | 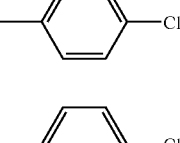 |
| 177 | 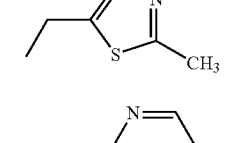 | 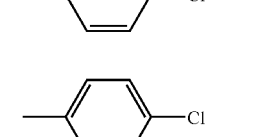 | 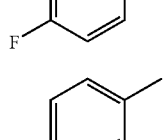 |
| 178 | 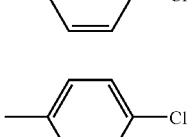 | 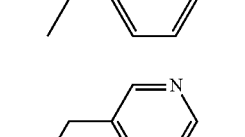 | 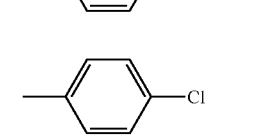 |
| 179 | 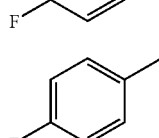 | 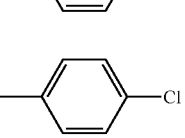 | 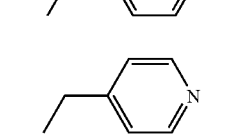 |
| 180 | 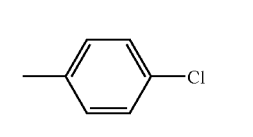 | 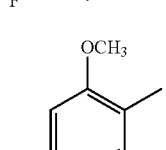 | 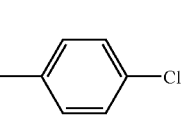 |

TABLE 1B-continued
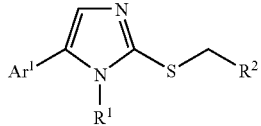
| Cpd No. | Ar¹ | R¹ | R² |
|---|---|---|---|
| 181 | 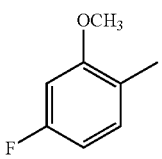 | 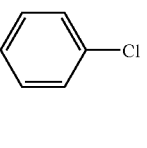 | 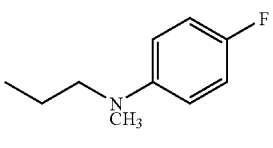 |
| 182 |  | 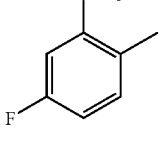 | 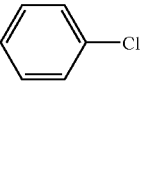 |
| 183 | 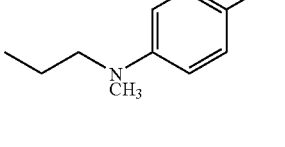 | 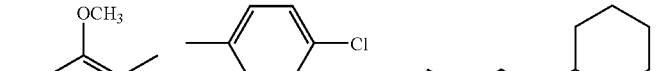 | 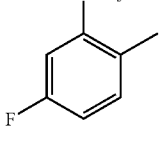 |
| 184 | 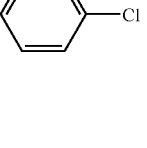 | 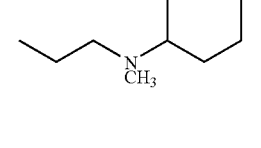 | 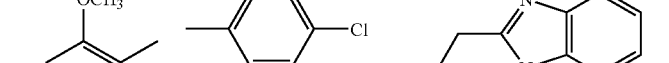 |
| 185 | 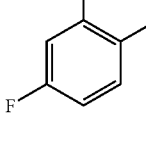 | 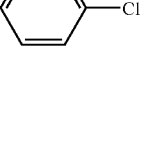 | 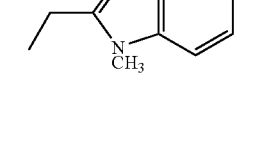 |
| 186 | 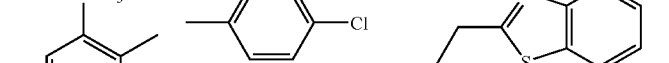 |  | 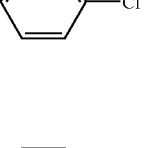 |
| 187 | 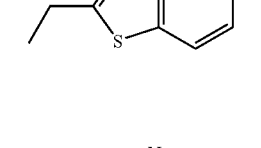 | 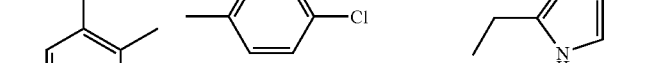 |  |
| 188 | 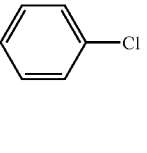 | 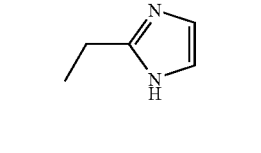 | 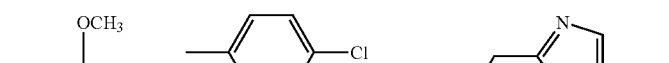 |

TABLE 1B-continued

| Cpd No. | Ar¹ | R¹ | R² |
|---|---|---|---|
| 189 | 4-fluoro-2-methoxy-phenyl (OCH₃ ortho, F para to attachment) | 4-Cl-phenyl | 2-pyridyl-ethyl |
| 190 | 4-fluoro-2-methoxy-phenyl | 4-Cl-phenyl | 3-pyridyl-ethyl |
| 191 | 4-fluoro-2-methoxy-phenyl | 4-Cl-phenyl | 4-pyridyl-ethyl |
| 192 | 4-fluoro-2-methyl-phenyl | 4-Cl-phenyl | 3-(pyrrolidin-1-yl)propyl |
| 193 | 4-fluoro-2-methyl-phenyl | 4-Cl-phenyl | 3-(piperidin-1-yl)propyl |
| 194 | 4-fluoro-2-methyl-phenyl | 4-Cl-phenyl | 3-[N-methyl-N-(4-fluorophenyl)amino]propyl |
| 195 | 4-fluoro-2-methyl-phenyl | 4-Cl-phenyl | 3-[N-methyl-N-(4-methoxyphenyl)amino]propyl |

TABLE 1B-continued
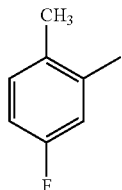
| Cpd No. | Ar¹ | R¹ | R² |
| --- | --- | --- | --- |
| 196 | 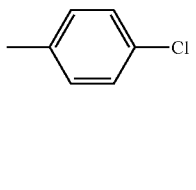 | 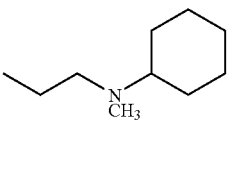 | 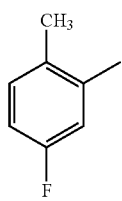 |
| 197 | 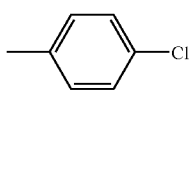 | 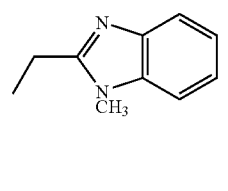 | 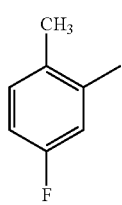 |
| 198 | 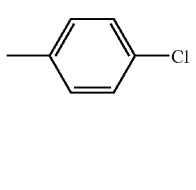 | 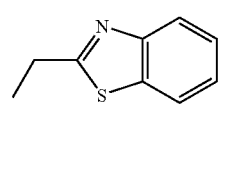 | 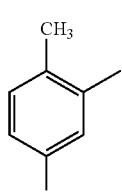 |
| 199 | 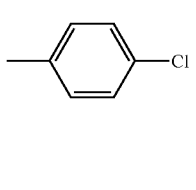 | 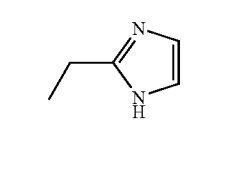 | 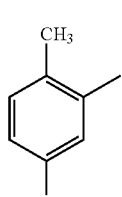 |
| 200 | 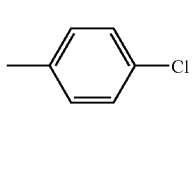 | 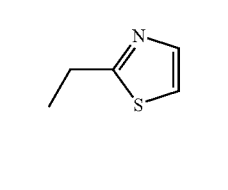 | 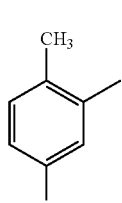 |
| 201 | 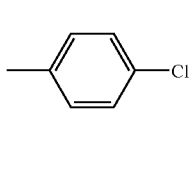 | 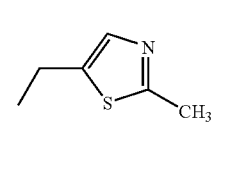 | 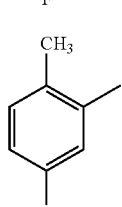 |
| 202 | 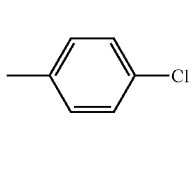 | 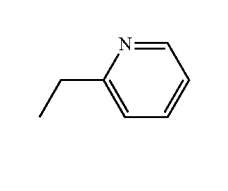 | |

TABLE 1B-continued
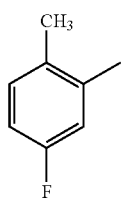
| Cpd No. | Ar¹ | R¹ | R² |
|---|---|---|---|
| 203 | 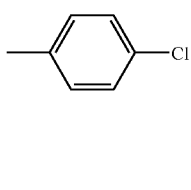 | 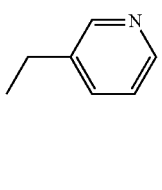 | 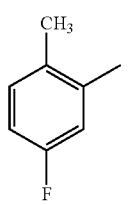 |
| 204 | 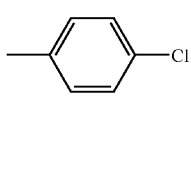 | 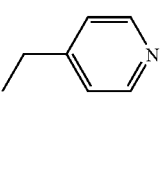 | 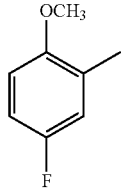 |
| 205 | 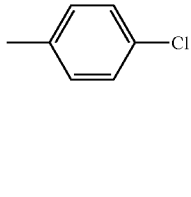 | 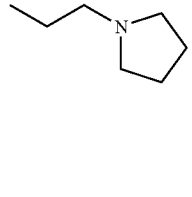 | 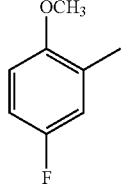 |
| 206 | 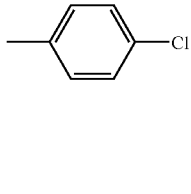 | 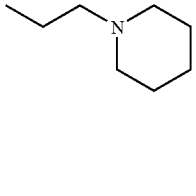 | 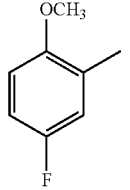 |
| 207 | 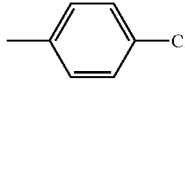 | 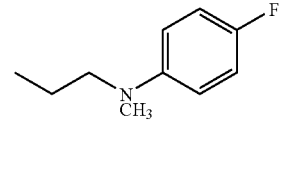 | 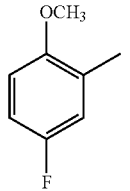 |
| 208 | 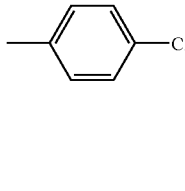 | | 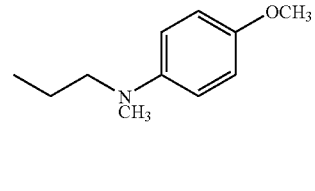 |

TABLE 1B-continued
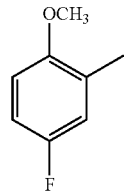
| Cpd No. | Ar¹ | R¹ | R² |
|---|---|---|---|
| 209 | 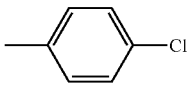 | 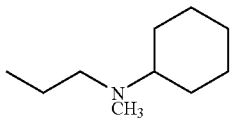 | 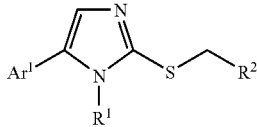 |
| 210 |  | 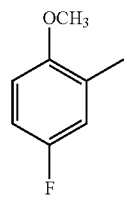 | 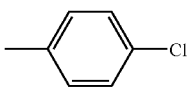 |
| 211 | 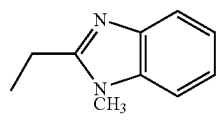 | 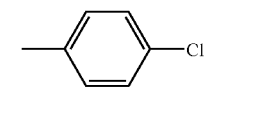 | 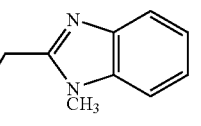 |
| 212 | 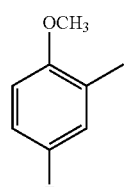 | 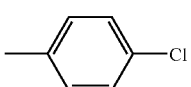 | 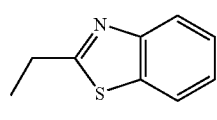 |
| 213 | 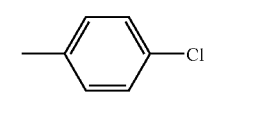 | 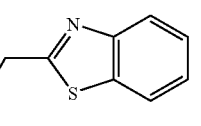 | 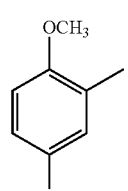 |
| 214 | 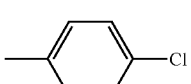 | 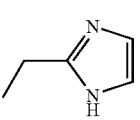 | 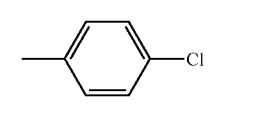 |
| 215 | 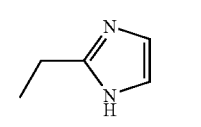 | 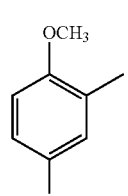 | 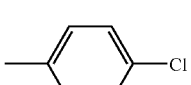 |

TABLE 1B-continued

| Cpd No. | Ar¹ | R¹ | R² |
|---|---|---|---|
| 216 | 4-fluoro-2-methylanisole | 4-chlorophenyl | 3-pyridylmethyl |
| 217 | 4-fluoro-2-methylanisole | 4-chlorophenyl | 4-pyridylmethyl |
| 218 | 4-fluorophenyl | 4-methylphenyl | (1H-benzimidazol-2-yl)methyl |
| 219 | 4-fluorophenyl | 6-methylpyridin-3-yl | (1H-benzimidazol-2-yl)methyl |
| 220 | 4-fluorophenyl | CH₃ | (1H-benzimidazol-2-yl)methyl |
| 221 | 4-fluorophenyl | cyclohexyl | (1H-benzimidazol-2-yl)methyl |
| 222 | 4-fluorophenyl | 4-chlorobenzyl | (1H-benzimidazol-2-yl)methyl |
| 223 | 4-fluorophenyl | 4-chlorophenyl | 3-[N-methyl-N-(pyridin-4-yl)amino]propyl |
| 224 | 4-fluorophenyl | 4-methylphenyl | 3-[N-methyl-N-(pyridin-4-yl)amino]propyl |

TABLE 1B-continued
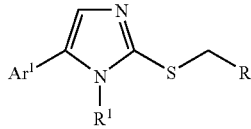
| Cpd No. | Ar¹ | R¹ | R² |
|---|---|---|---|
| 225 | 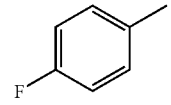 | 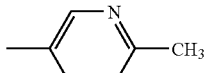 | 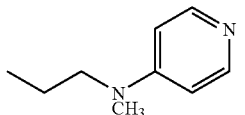 |
| 226 | 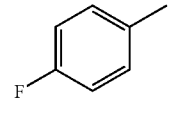 | CH₃ | 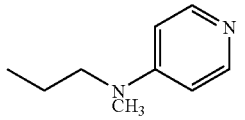 |
| 227 | 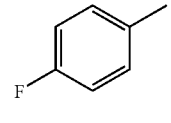 |  | 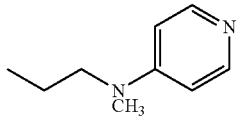 |
| 228 | 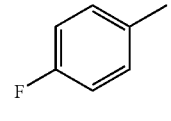 | 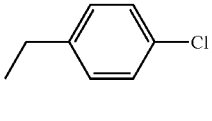 | 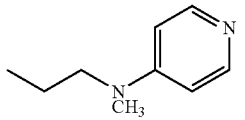 |
| 229 | 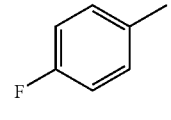 | 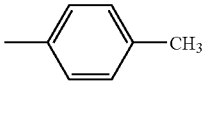 | 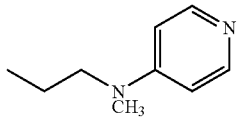 |
| 230 | 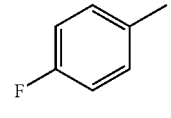 | 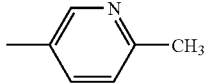 | 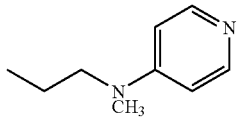 |
| 231 | 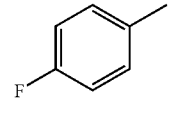 | CH₃ | 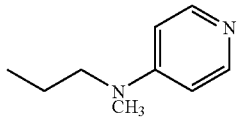 |
| 232 | 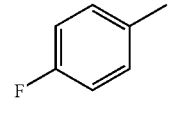 |  | 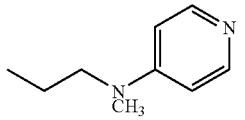 |
| 233 | 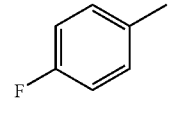 | 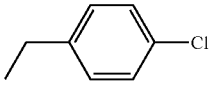 | 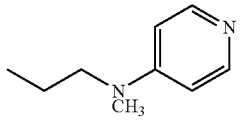 |

TABLE 1C

| Cpd No. | Ar¹ | R¹ | R² |
|---|---|---|---|
| 234 | 4-F-C₆H₄ | 4-MeO-C₆H₄ | -C(O)NHCH₂-(2-furyl) (propanamide linker) |
| 235 | 4-F-C₆H₄ | CH₃ | -C(O)NH-(4-F-C₆H₄) (propanamide linker) |
| 236 | C₆H₅ | CH₃ | -C(O)N(Et)₂ (propanamide linker) |
| 237 | 4-F-C₆H₄ | CH₃ | -C(O)NHCH₂-(2-furyl) (propanamide linker) |
| 238 | C₆H₅ | CH₃ | -C(O)NH-(5-ethyl-1,3,4-thiadiazol-2-yl) (propanamide linker) |
| 239 | C₆H₅ | Et | -C(O)NH-(5-ethyl-1,3,4-thiadiazol-2-yl) (propanamide linker) |
| 240 | 4-F-C₆H₄ | CH₃ | -C(O)NHCH₂Ph (propanamide linker) |
| 241 | C₆H₅ | CH₃ | -C(O)-(1,2,3,4-tetrahydroisoquinolin-2-yl) (propanoyl linker) |
| 242 | C₆H₅ | CH₃ | -C(O)NH-(3-HO-C₆H₄) (propanamide linker) |

TABLE 1C-continued
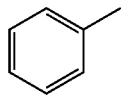
| Cpd No. | Ar¹ | R¹ | R² |
|---|---|---|---|
| 243 | 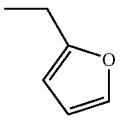 | 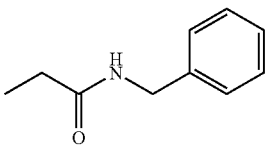 | 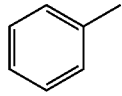 |
| 244 | 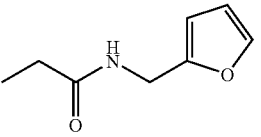 | CH₃ | 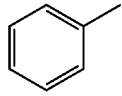 |
| 245 | 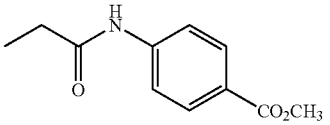 | CH₃ | 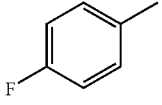 |
| 246 | 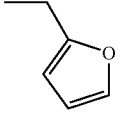 | 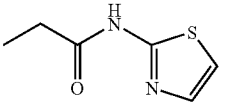 | 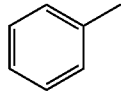 |
| 247 | 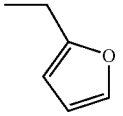 | 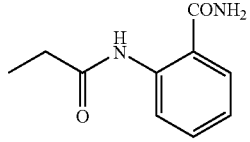 | 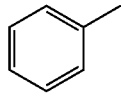 |
| 248 | 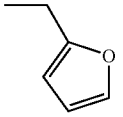 | 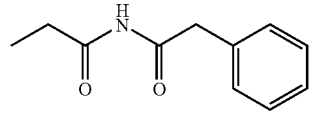 | 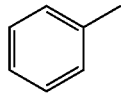 |
| 249 | 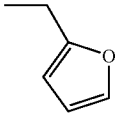 | 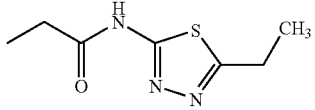 | 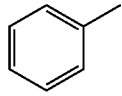 |
| 250 | 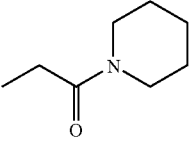 | CH₃ | 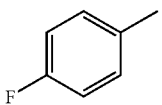 |
| 251 | 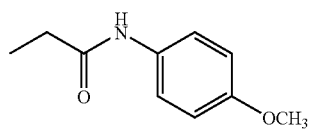 | CH₃ |  |

TABLE 1C-continued

| Cpd No. | Ar¹ | R¹ | R² |
|---|---|---|---|
| 252 | phenyl | Et | 1-propanoyl-1,2,3,4-tetrahydroquinoline |
| 253 | 4-fluorophenyl | CH₃ | N-(2-methoxyphenyl)propanamide |
| 254 | phenyl | CH₃ | N-(5-chloro-2-methoxyphenyl)propanamide |
| 255 | phenyl | CH₃ | N-(4-ethoxyphenyl)propanamide |
| 256 | phenyl | CH₃ | N-(4-bromophenyl)propanamide |
| 257 | phenyl | CH₃ | N,N-diphenylpropanamide |
| 258 | phenyl | CH₃ | N-(5-chloro-2-methylphenyl)propanamide |
| 259 | phenyl | CH₃ | N-(2-methyl-4-nitrophenyl)propanamide |

TABLE 1C-continued

Structure: Ar¹ attached to imidazole ring (with N, N) and S-R² group; N bearing R¹

| Cpd No. | Ar¹ | R¹ | R² |
|---|---|---|---|
| 260 | phenyl | CH₃ | -CH₂C(O)NH-(4-Cl-phenyl) |
| 261 | phenyl | Et | -CH₂C(O)NH-(thiazol-2-yl) |
| 262 | phenyl | CH₃ | -CH₂C(O)NH-(2-NO₂-phenyl) |
| 263 | 4-F-phenyl | 4-OCH₃-phenyl | -CH₂C(O)NH₂ |
| 264 | phenyl | phenyl | -CH₂C(O)NH-(6-OEt-benzothiazol-2-yl) |
| 265 | phenyl | 4-OCH₃-phenyl | -CH₂C(O)NH-(3,5-diCH₃-phenyl) |
| 266 | phenyl | 4-OCH₃-phenyl | -CH₂C(O)NH-(3,5-diCH₃-phenyl) |
| 267 | 4-F-phenyl | 4-OCH₃-phenyl | -CH₂C(O)NH-(thiazol-2-yl) |

Ion channel-modulating compounds can be identified through both in vitro (e.g., cell and non-cell based) and in vivo methods. Representative examples of these methods are described in the Examples herein.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The compounds delineated herein can be synthesized using conventional methods, as illustrated in Scheme 1. Ar¹, R¹ and R² are defined as in any of the formulae herein.

Scheme 1

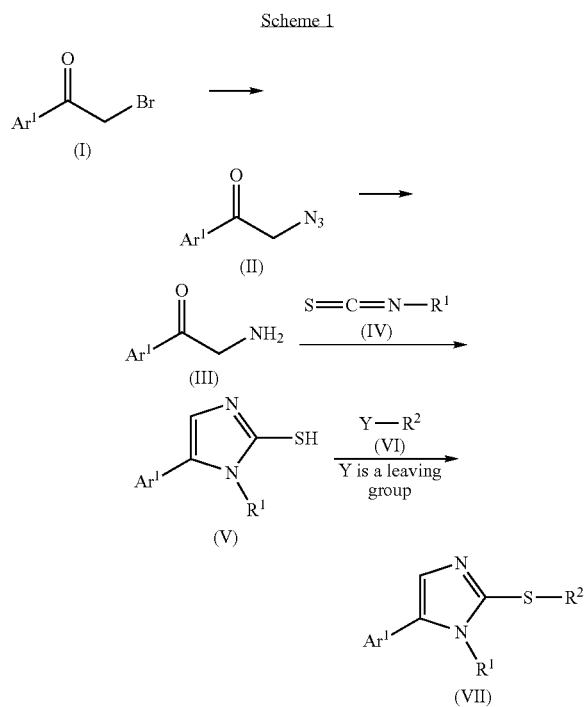

Treatment of the bromomethyl ketone (I) in solvent, such as DMSO, with sodium azide provides the azidomethyl ketone (II). Treatment of (II) with reducing conditions, such as palladium on carbon in aqueous HCl and $H_2$ atmosphere, provides the amine (III). The reaction of (III) and isothiocyanate (IV) under basic conditions, such as sodium hydrogencarbonate, in a solvent, such as ethanol, provides thioimidazole (V). The reaction of (V) and (VI) under basic condition, such as potassium carbonate, provides imidazole (VII).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2nd. Ed., Wiley-VCH Publishers (1999); T. W. Greene and P. G. M. Wuts, *Protective Groups in Organic Synthesis,* 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214; Sinkula, A. A.; Yalkowsky. *Journal of Pharmaceutical Sciences* 1975, 64, 181-210; Verbiscar, A. J.; Abood, L. G *Journal of Medicinal Chemistry* 1970, 13, 1176-1179; Stella, V. J.; Himmelstein, K. J. *Journal of Medicinal Chemistry* 1980, 23, 1275-1282; Bodor, N.; Kaminski, J. J. *Annual Reports in Medicinal Chemistry* 1987, 22, 303-313.

The compounds of this invention may be modified by appending appropriate functionalities to enhance selective biological properties. Such modifications are known in the art and include those which increase biological penetration into a given biological compartment (e.g., blood, lymphatic system, nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

The compositions delineated herein include the compounds of the formulae delineated herein, as well as additional therapeutic agents if present, in amounts effective for achieving a modulation of disease or disease symptoms, including ion channel-mediated disorders or symptoms thereof. References which include examples of additional therapeutic agents are: 1) *Burger's Medicinal Chemistry & Drug Discovery* 6$^{th}$ edition, by Alfred Burger, Donald J. Abraham, ed., Volumes 1 to 6, Wiley Interscience Publication, NY, 2003; 2) *Ion Channels and Disease* by Francis M. Ashcroft, Academic Press, NY, 2000; and 3) *Calcium Antagonists in Clinical Medicine* 3$^{rd}$ edition, Murray Epstein, MD, FACP, ed., Hanley & Belfus, Inc., Philadelphia, Pa., 2002. Additional therapeutic agents include but are not limited to agents for the treatment of cardiovascular disease (e.g., hypertension, angina, etc), metabolic disease (e.g., syndrome X, diabetes, obesity), pain (e.g., acute pain, inflammatory pain, neuropathic pain, migraine, etc), renal or genito-urinary disease (e.g, glomerular nephritis, urinary incontinence, nephrotic syndrome), abnormal cell growth (e.g., oncology, fibrotic diseases), nervous system disease (e.g., epilepsy, stroke, migraine, traumatic brain injury or neuronal disorders, etc.), respiratory disease (e.g., asthma, COPD, pulmonary hypertension) and their disease symptoms. Examples of additional therapeutic agents for treatment of cardiovascular disease and disease symptoms include but are not limited to antihypertensive agents, ACE inhibitors, angiotensin II receptor antagonists, statins, β-blockers, antioxidants, anti-inflammatory drugs, anti-thrombotics, anti-coagulants or antiarrythmics. Examples of additional therapeutic agents for treatment of metabolic disease and disease symptoms include but are not limited to ACE inhibitors, angiotensin II antagonists, fibrates, thiazolidinediones or sulphonylurea anti-diabetic drugs. Examples of additional therapeutic agents for treatment of pain and its symptoms include but are not limited to non-steroidal anti-inflammatory drugs ("NSAIDS", e.g., aspirin, ibuprofen, flumizole, acetaminophen, etc.), opioids (e.g., morphine, fentanyl, oxycodone), and agents such as gabapentin, ziconitide, tramadol, dextromethorphan, carbamazepine, lamotrigine, baclofen or capsaicin. Examples of additional therapeutic agents for treatment of renal and/or genitorurinary syndromes and their symptoms include but are not limited to alpha-1 adrenergic antagonists (e.g., doxazosin), anti-muscarinics (e.g., tolterodine), norepinephrine/serotonin reuptake inhibitors (e.g., duloxetine), tricyclic antidepressants (e.g., doxepin, desipramine) or steroids. Examples of additional therapeutic agents for treatment of abnormal cell growth syndromes and their symptoms include but are not limited to anti-cytokine therapies (e.g., anti-TNF and anti-IL-1 biologics, p38 MAPK inhibitors), endothelin-1 antagonists or stem cell therapies (e.g., progenitor cells). Examples of additional therapeutic agents for treatment of stroke disease and disease symptoms include but are not limited to neuroprotective agents and anticoagulants (e.g., alteplase (TPA), abciximab). Examples of additional therapeutic agents for treatment of epilepsy and its symptoms include but are not limited to GABA analogs, hydantoins, barbiturates, phenyl triazines, succinimides, valproic acid, carbamazepine, falbamate, and leveracetam. Examples of additional therapeutic agents for the treatment of migraine include but are not limited to serotonin/5-HT receptor agonist (e.g., sumatriptan, etc.). Examples of additional therapeutic agents for treatment of respiratory diseases and their symptoms include but are not limited to anticholinergics (e.g., tiotropium), steroids, anti-inflammatory agents, anti-cytokine agents or PDE inhibitors.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The invention will be further described in the following examples. It should be understood that these examples are for illustrative purposes only and are not to be construed as limiting this invention in any manner.

EXAMPLE 1

Oocyte Assay

Representative compounds of the formulae herein are screened for activity against calcium channel targets in an assay essentially as described in *Neuron* January 1997, 18(11): 153-166, Lin et. al.; *J. Neurosci.* Jul. 1, 2000, 20(13):4768-75, J. Pan and D. Lipsombe; and *J. Neurosci.*, Aug. 15, 2001, 21(16):5944-5951, W. Xu and D. Lipscombe, using *Xenopus oocyte* heterologeous expression system. The assay is performed on various calcium channels (e.g., $Ca_v2.2$subfamily) whereby the modulation of the calcium channel is measured for each compound. Table 2 contains $IC_{50}$'s for representative compounds disclosed in the invention.

TABLE 2

| Example | $IC_{50}$ (μM) |
|---------|----------------|
| 2       | 6.63           |
| 4       | 5.70           |
| 234     | 5.4            |

EXAMPLE 2

HEK Assay

HEK-293T/17 cells are transiently transfected in a similar manner as described in FuGENE 6 Package Insert Version 7, April 2002, Roche Applied Science, Indianapolis, Ind. The cells are plated at $2.5 \times 10^5$ cells in 2 mL in a 6-well plate in incubator for one night and achieve a 30~40% confluence. In a small sterile tube, add sufficient serum-free medium as diluent for FuGENE Transfection Reagent (Roche Applied Science, Indianapolis, Ind.), to a total volume of 100 μL. Add 3 μL of FuGENE 6 Reagent directly into this medium. The mixture is tapped gently to mix. 2 μg of DNA solution (0.8-2.0 μg/μL) is added to the prediluted FuGENE 6 Reagent from above. The DNA/Fugene 6 mixture is gently pipeted to mix the contents and incubated for about 15 minutes at room temperature. The complex mixture is then added to the HEK-293T/17 cells, distributing it around the well, and swirled to ensure even dispersal. The cells are returned to the incubator for 24 hrs. The transfected cells are then replated at density $2.5 \times 10^5$ in a 35 mm dish with 5 glass coverslips and grow in low serum(1%) media for 24 hrs. Coverslips with isolated cells are then transferred into chamber and calcium channel (e.g., L-type, N-type, etc.) current or other currents for counter screening are recorded from the transiently transfected HEK-293T/1 7 cells.

The whole-cell voltage clamp configuration of the patch clamp technique is employed to evaluate voltage-dependent calcium currents essentially as described by Thompson and Wong (1991) *J. Physiol.*, 439: 671-689. To record calcium channel (e.g., L-type, N-type, etc.) currents for evaluation of inhibitory potency of compounds (steady-state concentration-response analysis), five pulses of 20-30 ms voltage steps to about +10 mV (the peak of the current voltage relationship) are delivered at five Hz every 30 second from a holding potential at −100 mV. Compound evaluations were carried out essentially as described by Sah D W and Bean B P (1994) *Mol Pharmacol.* 45(1):84-92. Table 3 contains $IC_{50}$'s for representative compounds.

TABLE 3

| Example | $IC_{50}$ (μM) |
|---------|----------------|
| 7       | 0.793          |
| 8       | 0.187          |
| 13      | 0.328          |

EXAMPLE 3

Formalin Test

Representative compounds of the formulae herein are screened for activity in the formalin test. The formalin test is widely used as a model of acute and tonic inflammatory pain (Dubuisson & Dennis, 1977 *Pain* 4:161-174; Wheeler-Aceto et al, 1990, *Pain* 40:229-238; Coderre et al, 1993, *Pain* 52:259-285). The test involves the administration to the rat hind paw of a dilute formalin solution followed by monitoring behavioral signs (i.e., flinching, biting and licking) during the "late phase" (11 to 60 minutes post injection) of the formalin response which reflects both peripheral nerve activity and central sensitization. Male, Sprague-Dawley rats (Harlan, Indianapolis, Ind.) weighing approximately 225-300 g are used with an n=6-8 for each treatment group.

Depending on pharmacokinetic profile and route of administration, vehicle or a dose of test compound is administered to each rat by the intraperitoneal or oral route 30-120 minutes prior to formalin. Each animal is acclimated to an experimental chamber for 60 minutes prior to formalin administration, which is 50 μL of a 5% solution injected subcutaneously into the plantar surface of one hind paw using a 300 μL microsyringe and a 29 gauge needle. A mirror is angled behind the chambers to enhance the views of the animals' paws. The number of flinches (paw lifts with or without rapid paw shaking) and the time spent biting and/or licking the injured hind paw are recorded for each rat for 2 continuous minutes every 5 minutes for a total of 60 minutes after formalin administration. A terminal blood sample is harvested for analysis of plasma compound concentrations. Between groups comparisons of the total number of flinches or time spent biting and/or licking during the early or late phase are conducted using one-way analysis of variance (ANOVA).

EXAMPLE 4

Representative compounds of the formulae herein were evaluated for activity against calcium channel targets.

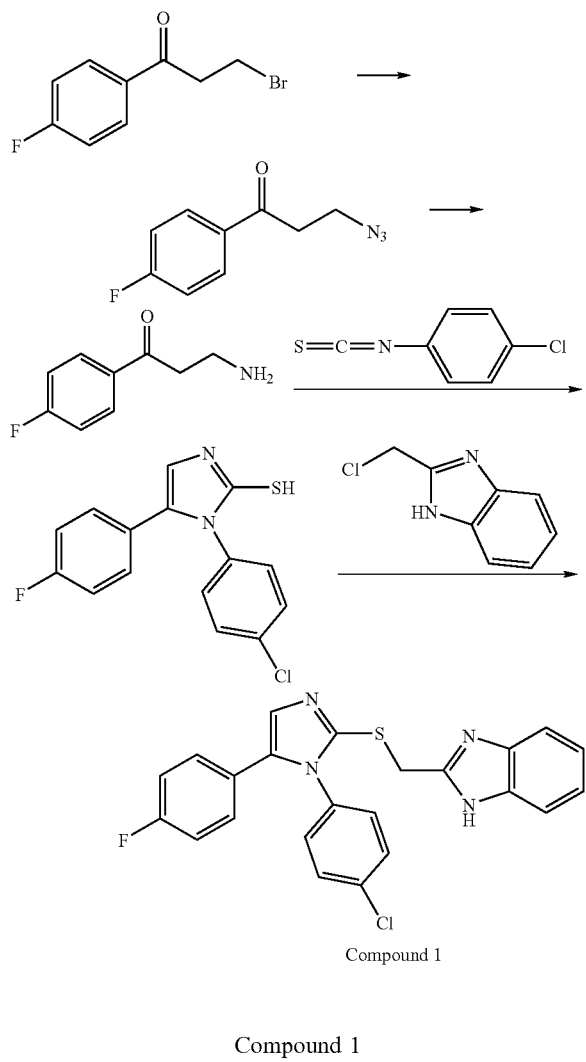

Compound 1

2-[1-(4-Chloro-phenyl)-5-(4-fluoro-phenyl)-1H-imidazol-2-ylsulfanylmethyl]-1H-benzoimidazole Part 1. Preparation of
2-Azido-1-(4-fluoro-phenyl)-ethanone A solution of 2-bromo-1-(4-fluoro-phenyl)-ethanone (2.5 g, 11.5 mmol) in DMSO (15 mL) at 10° C. was vigorously stirred and sodium azide (0.94 g, 14.4 mmol) was added. The mixture was stirred for 1 hour then quenched with water (20 mL) and extracted with ethyl acetate (2×25 mL). The combined organic layers were washed with water (25 mL) and brine (25 mL), dried over anhydrous sodium sulfate, filtered and concentrated under reduce pressure to give 2-azido-1-(4-fluoro-phenyl)-ethanone (1.7 g, 9.3 mmol) as a viscous yellow-red liquid.

Part 2. Preparation of
2-Amino-1-(4-fluoro-phenyl)-ethanone
hydrochloride

To a solution of 2-azido-1-(4-fluoro-phenyl)-ethanone (8.0 g, 44.7 mmol) in ethanol (125 mL) was added concentrated aqueous HCl (6 mL) and 10% Pd/C (10 mol %). The mixture was stirred under hydrogen ($H_2$) atmosphere at 45 psi for 1 hour. The mixture was filtered through celite and the celite cake was washed with copious amounts of methanol. The solvent was under reduce pressure and the semi-solid was triturated with diethyl ether, filtered and dried to give 2-amino-1-(4-fluoro-phenyl)-ethanone hydrochloride (5.0 g, 26.5 mmol) as a white crystalline solid.

Part 3. Preparation of 1-(4-Chloro-phenyl)-5-(4-fluoro-phenyl)-1H-imidazole-2-thiol A mixture of 2-amino-1-(4-fluoro-phenyl)-ethanone hydrochloride (5.0 g, 26.5 mmol), 4-chlorophenyl isothiocyanate (4.49 g, 26.5 mmol) and sodium hydrogencarbonate (3.3 g, 39.7 mmol) in ethanol (100 mL) was heated at 90° C. for 2 hours. The solvent was removed under reduce pressure. The resulting residue was re-suspended in aqueous 1N sodium hydroxide (50 mL) and heated at 100° C. overnight. The hot mixture was filtered, cooled and carefully acidifed with aqueous 6N HCl. The resulting mixture was filtered to give 1-(4-chloro-phenyl)-5-(4-fluoro-phenyl)-1H-imidazole-2-thiol (8.0 g, 26.3 mmol) as a yellow solid after drying.

Part 4. Preparation of 2-[1-(4-Chloro-phenyl)-5-(4-fluoro-phenyl)-1H-imidazol-2-yl-sulfanylmethyl]-1H-benzoimidazole A mixture of 1-(4-chloro-phenyl)-5-(4-fluoro-phenyl)-1H-imidazole-2-thiol (4.0 g, 13.2 mmol), 2-(chloromethyl) benzimidazole (2.2 g, 13.2 mmol) and potassium carbonate (5.5 g, 39.6 mmol) in acetone (50 mL) was heated at 75° C. until all starting materials were consumed. The mixture was cooled and the solvent was removed under reduce pressure. The resulting residue was partitioned in 1:1:1 water/ethyl acetate/hexane. The brown solid was filtered, dried and re-suspended in minimal amount of methanol. The methanolic mixture was filtered and dried to obtain a white solid. The solid was re-suspended in methanol and treated with ethereal 2N HCl until a solution persisted. The solution was diluted with a large amount of diethyl ether to promote precipitation, filtered and dried to give 2-[1-(4-chloro-phenyl)-5-(4-fluoro-phenyl)-1H-imidazol-2-yl-sulfanylmethyl]-1H-benzoimidazole (3.5 g, 7.4 mmol) as a white solid.

Compounds in the tables herein are prepared in a manner similar as described above and in the general schemes.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula (I) or pharmaceutical salt thereof

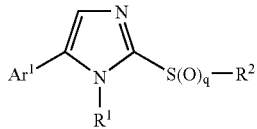

I wherein,
- $Ar^1$ is cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;
- $R^1$ is $Ar^2$ or lower alkyl optionally substituted with $Ar^2$;
- $Ar^2$ is independently selected from cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;
- q is 0, 1 or 2;
- each $R^2$ is independently selected from $(CH_2)_mCO_2R^3$, $(CH_2)_mCOAr^3$, $(CH_2)_mCONR^3R^4$, $(CH_2)_mAr^3$, $(CH_2)_3Ar^3$, $(CH_2)_nNR^3R^4$ or $(CH_2)_nOR^4$;
- each $R^3$ is independently selected from H, or lower alkyl;
- each $R^4$ is independently selected from H, lower alkyl or $(CH_2)_pAr^3$;
- each $Ar^3$ is cycloalkyl, aryl, heterocyclyl, or heteroaryl, each optionally substituted with one or more substituents, with the proviso that $Ar^3$ is not piperidinyl, tetrahydroquinolinyl or tetrahydroisoquinolinyl;
- each m is 1 or 2;
- each n is 2 or 3;
- each p is 0 or 1;
- each substituent for $Ar^1$, $Ar^2$ and $Ar^3$ is independently selected from halogen, CN, $NO_2$, $OR^5$, $SR^5$, $S(O)_2OR^5$, $NR^5R^6$, cycloalkyl, $C_1$-$C_2$ perfluoroalkyl, $C_1$-$C_2$ perfluoroalkoxy, 1,2-methylenedioxy, $C(O)OR^5$, $C(O)NR^5R^6$, $OC(O)NR^5R^6$, $NR^5C(O)NR^5R^6$, $C(NR^6)NR^5R^6$, $NR^5C(NR^6)NR^5R^6$, $S(O)_2NR^5R^6$, $R^7$, $C(O)R^7$, $NR^5C(O)R^7$, $S(O)R^7$, or $S(O)_2R^7$;
- each $R^5$ is independently selected from hydrogen or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;
- each $R^6$ is independently selected from hydrogen, $(CH_2)_pAr^4$, or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;
- each $R^7$ is independently selected from $(CH_2)_pAr^4$ or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl; and 0
- each $Ar^4$ is independently selected from $C_3$-$C_6$ cycloalkyl, aryl or heteroaryl, each optionally substituted with one to three substituents independently selected from halogen, OH, $C_1$-$C_4$ alkoxy, $NH^2$, $C_1$-$C_4$ alkylamino, $C_1$-$C_4$ dialkylamino or 1,2-methylenedioxy.

2. A compound of formula (I) and pharmaceutical salts and esters thereof

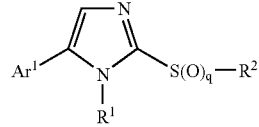

I wherein,
- $Ar^1$ is cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;
- $R^1$ is $Ar^2$ or lower alkyl optionally substituted with $Ar^2$;
- $Ar^2$ is independently selected from cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;
- q is 0;
- each $R^2$ is independently selected from $(CH_2)_mCO_2R^3$, $(CH_2)_mCOAr^3$, $(CH_2)_mCONR^3R^4$, $(CH_2)_mAr^3$, $(CH_2)_3Ar^3$, $(CH_2)_nNR^3R^4$ or $(CH_2)_nOR^4$;
- each $R^3$ is independently selected from H, or lower alkyl;
- each $R^4$ is independently selected from H, lower alkyl or $(CH_2)_pAr^3$;
- each $Ar^3$ is cycloalkyl, aryl, heterocyclyl, or heteroaryl, each optionally substituted with one or more substituents, with the proviso that $Ar^3$ is not piperidinyl, tetrahydroquinolinyl or tetrahydroisoquinolinyl;
- each m is 1 or 2;
- each n is 2 or 3;
- each p is 0 or 1;
- each substituent for $Ar^1$, $Ar^2$ and $Ar^3$ is independently selected from halogen, CN, $NO_2$, $OR^5$, $SR^5$, $S(O)_2OR^5$, $NR^5R^6$, cycloalkyl, $C_1$-$C_2$ perfluoroalkyl, $C_1$-$C_2$ perfluoroalkoxy, 1,2-methylenedioxy, $C(O)OR^5$, $C(O)NR^5R^6$, $OC(O)NR^5R^6$, $NR^5C(O)NR^5R^6$, $C(NR^6)NR^5R^6$, $NR^5C(NR^6)NR^5R^6$, $S(O)_2NR^5R^6$, $R^7$, $C(O)R^7$, $NR^5C(O)R^7$, $S(O)R^7$, or $S(O)_2R^7$;
- each $R^5$ is independently selected from hydrogen or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^6$ is independently selected from hydrogen, $(CH_2)_p$ $Ar^4$, or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^7$ is independently selected from $(CH_2)_p Ar^4$ or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl; and each $Ar^4$ is independently selected from $C_3$-$C_6$ cycloalkyl, aryl or heteroaryl, each optionally substituted with one to three substituents independently selected from halogen, OH, $C_1$-$C_4$ alkoxy, $NH_2$, $C_1$-$C_4$ alkylamino, $C_1$-$C_4$ dialkylamino or 1,2-methylenedioxy.

3. A compound of formula (I) and pharmaceutical salt thereof

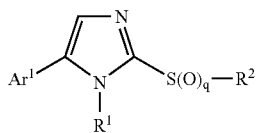

I wherein,
$Ar^1$ is cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;

$R^1$ is $Ar^2$ or lower alkyl optionally substituted with $Ar^2$;

$Ar^2$ is independently selected from cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;

q is 1;

each $R^2$ is independently selected from $(CH_2)_m CO_2 R^3$, $(CH_2)_m COAr^3$, $(CH_2)_m CONR^3 R^4$, $(CH_2)_m Ar^3$, $(CH_2)_3 Ar^3$, $(CH_2)_n NR^3 R_4$ or $(CH_2)_n OR^4$;

each $R^3$ is independently selected from H, or lower alkyl;

each $R^4$ is independently selected from H, lower alkyl or $(CH_2)_p Ar^3$;

each $Ar^3$ is cycloalkyl, aryl, heterocyclyl, or heteroaryl, each optionally substituted with one or more substituents, with the proviso that $Ar^3$ is not piperidinyl, tetrahydroquinolinyl or tetrahydroisoquinolinyl;

each m is 1 or 2;

each n is 2 or 3;

each p is 0 or 1;

each substituent for $Ar^1$, $Ar^2$ and $Ar^3$ is independently selected from halogen, CN, $NO_2$, $OR^5$, $SR^5$, $S(O)_2 OR^5$, $NR^5 R^6$, cycloalkyl, $C_1$-$C_2$ perfluoroalkyl, $C_1$-$C_2$ perfluoroalkoxy, 1,2-methylenedioxy, $C(O)OR^5$, $C(O)NR^5R^6$, $OC(O)NR^5R^6$, $NR^5C(O)NR^5R^6$, $C(NR^6)NR^5R^6$, $NR^5C(NR^6)NR^5R^6$, $S(O)_2NR^5R^6$, $R^7$, $C(O)R^7$, $NR^5C(O)R^7$, $S(O)R^7$, or $S(O)_2R^7$;

each $R^5$ is independently selected from hydrogen or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^6$ is independently selected from hydrogen, $(CH_2)_p$ $Ar^4$, or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl;

each $R^7$ is independently selected from $(CH_2)_p Ar^4$ or lower alkyl optionally substituted with one or more substituent independently selected from halogen, OH, $C_1$-$C_4$ alkoxy, $NH_2$, $C_1$-$C_4$ alkylamino, $C_1$-$C_4$ dialkylamino or $C_3$-$C_6$ cycloalkyl; and each $Ar^4$ is independently selected from $C_3$-$C_6$ cycloalkyl, aryl or heteroaryl, each optionally substituted with one to three substituents independently selected from halogen, OH, $C_1$-$C_4$ alkoxy, $NH_2$, $C_1$-$C_4$ alkylamino, $C_1$-$C_4$ dialkylamino or 1,2-methylenedioxy.

4. A compound of formula (I) and pharmaceutical salt thereof

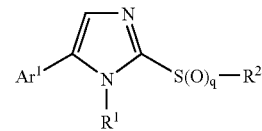

I wherein,
$Ar^1$ is cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;

$R^1$ is $Ar^2$ or lower alkyl optionally substituted with $Ar^2$;

$Ar^2$ is independently selected from cycloalkyl, aryl, heterocyclyl or heteroaryl, each of which may be optionally substituted with one or more substituents selected from the group consisting of H, halogen, amino, hydroxy, cyano, nitro, carboxylate, alkyl, alkenyl, alkynyl, cycloalkyl, cyclohexyl, alkoxy, mono and di-alkyl amino, phenyl, carboxamide, haloalkyl, haloalkoxy, and alkanoyl;

q is 2;

each $R^1$ is independently selected from $(CH_2)_m CO_2 R^3$, $(CH_2)_m COAr^3$, $(CH_2)_m CONR^3 R^4$, $(CH_2)_m Ar^3$, $(CH_2)_3 Ar^3$, $(CH_2)_n NR^3 R^4$ or $(CH_2)_n OR^4$;

each $R^3$ is independently selected from H, or lower alkyl;

each $R^4$ is independently selected from H, lower alkyl or $(CH_2)_p Ar^3$;

each $Ar^3$ is cycloalkyl, aryl, heterocyclyl, or heteroaryl, each optionally substituted with one or more substituents, with the proviso that $Ar^3$ is not piperidinyl, tetrahydroquinolinyl or tetrahydroisoquinolinyl;

each m is 1 or 2;

each n is 2 or 3;

each p is 0 or 1;

each substituent for $Ar^1$, $Ar^2$ and $Ar^3$ is independently selected from halogen, CN, $NO_2$, $OR^5$, $SR^5$, $S(O)_2 OR^5$, $NR^5 R^6$, cycloalkyl, $C_1$-$C_2$ perfluoroalkyl, $C_1$-$C_2$ perfluoroalkoxy, 1,2-methylenedioxy, $C(O)OR^5$, $C(O)NR^5R^6$, $OC(O)NR^5R^6$, $NR^5C(O)NR^5R^6$, $C(NR^6)$ NR$^5$R$^6$, NR$^5$C(NR)NR$^5$R$^6$ S(O)$_2$NR$^5$R$^6$, R$^7$, C(O)R$^7$, NR$^5$C(O)R$^7$, S(O)R$^7$, or S(O)$_2$R$^7$;

each R$^5$ is independently selected from hydrogen or lower alkyl optionally substituted with one or more substituent independently selected from halogen, OH, C$_1$-C$_4$ alkoxy, NH$_2$, C$_1$-C$_4$ alkylamino, C$_1$-C$_4$ dialkylamino or C$_3$-C$_6$ cycloalkyl;

each R$^6$ is independently selected from hydrogen, (CH$_2$)$_p$Ar$^4$, or lower alkyl optionally substituted with one or more substituent independently selected from halogen, OH, C$_1$-C$_4$ alkoxy, NH$_2$, C$_1$-C$_4$ alkylamino, C$_1$-C$_4$ dialkylamino or C$_3$-C$_6$ cycloalkyl;

each R$^7$ is independently selected from (CH$_2$)$_p$Ar$^4$ or lower alkyl optionally substituted with one or more substituent independently selected from halogen, OH, C$_1$-C$_4$ alkoxy, NH$_2$, C$_1$-C$_4$ alkylamino, C$_1$-C$_4$ dialkylamino or C$_3$-C$_6$ cycloalkyl; and each Ar$^4$ is independently selected from C$_3$-C$_6$ cycloalkyl, aryl or heteroaryl, each optionally substituted with one to three substituents independently selected from halogen, OH, C$_1$-C$_4$ alkoxy, NH$_2$, C$_1$-C$_4$ alkylamino, C$_1$-C$_4$ dialkylamino or 1,2-methylenedioxy.

5. A compound of claim 1, wherein R$^2$ is (CH$_2$)$_m$CO$_2$R$^3$, (CH$_2$)$_m$COAr$^3$, or (CH$_2$)$_m$CONR$^3$R$^4$, and m is 2.

6. A compound of claim 1, wherein R$^1$ is Ar$^2$ or lower alkyl substituted with Ar$^2$, R$^2$ is (CH$_2$)$_m$Ar$^3$, and m is 1, with the proviso that R$^1$ is not furylmethyl or tetra hydrofurylmethyl.

7. A compound of claim 1, wherein R$^1$ is Ar$^2$ or lower alkyl optionally substituted with Ar$^2$, R$^2$ is (CH$_2$)$_m$Ar$^3$, and m is 2, with the proviso that R$^1$ is not furylmethyl or tetrahydrofurylmethyl.

8. A compound of claim 1, wherein Ar$^1$ and R$^1$ are each an optionally substituted aryl, and R$^2$ is independently selected from (CH$_2$)$_m$Ar$^3$, (CH$_2$)$_3$Ar$^3$, (CH$_2$)$_n$NR$^3$R$^4$ or (CH$_2$)$_n$OR$^4$.

9. A compound of claim 8, wherein each R$^2$ is independently selected from (CH$_2$)$_m$Ar$^3$, and each Ar$^3$ is heteroaryl optionally substituted with one or more substituents.

10. A compound of claim 8, wherein Ar$^3$ is heteroaryl having a five-membered ring of carbon atoms and 1, 2 or 3 heteroatoms selected from N, O and S, optionally substituted with one or more substituents.

11. A compound of claim 8, wherein Ar$^3$ is pyrrolidinyl, pyrazolyl, imidazolyl, thioimidazolyl, benzimidazolyl, or benzthioimidazolyl, each optionally substituted with one or more substituents.

12. The compound of claim 1, wherein the compound is one of those delineated in Tables 1A, 1B and 1C, wherein Tables 1A, 1B, and 1C are as follows:

TABLE 1A

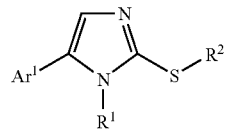

| Cpd. No. | Ar$^1$ | R$^1$ | R$^2$ |
|---|---|---|---|
| 1 | 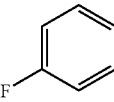 | 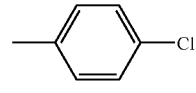 | 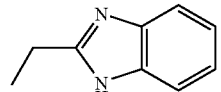 |
| 2 | 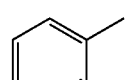 | 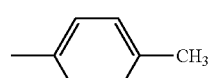 | 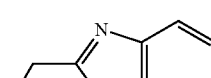 |
| 3 | 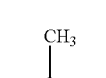 | 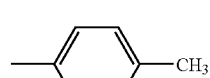 | 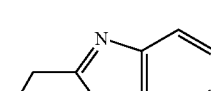 |
| 4 | 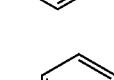 | 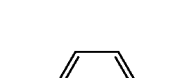 | 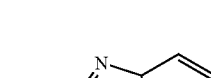 |
| 5 | 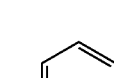 | 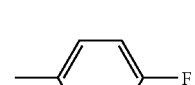 | 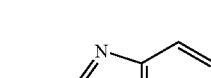 |

TABLE 1A-continued
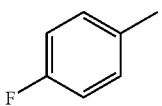
| Cpd. No. | Ar¹ | R¹ | R² |
|---|---|---|---|
| 6 | 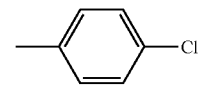 | 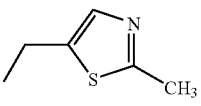 | 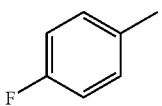 |
| 7 | 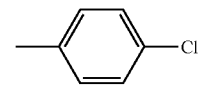 | 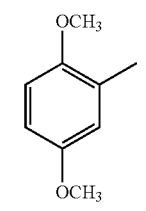 | 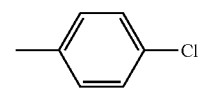 |
| 8 | 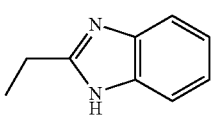 | 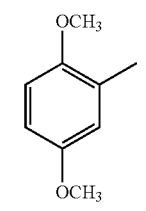 | 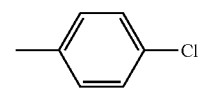 |
| 9 | 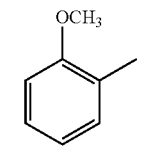 | 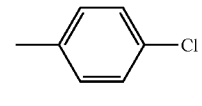 | 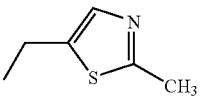 |
| 10 | 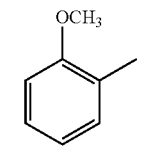 | 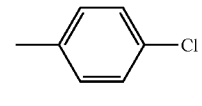 | 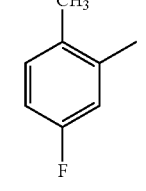<br>Sulfur is oxidized to Sulfoxide |
| 11 | 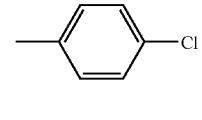 | Et | 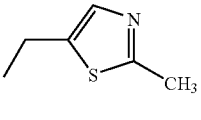 |
| 12 | 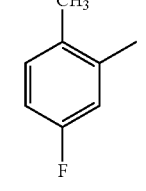 | 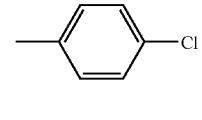 | 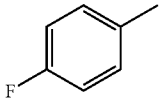 |
| 13 | 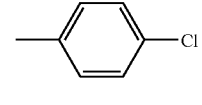 | 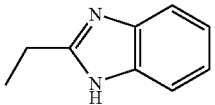 | 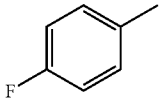 |

TABLE 1A-continued
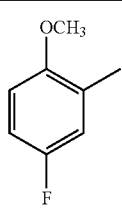
| Cpd. No. | Ar¹ | R¹ | R² |
|---|---|---|---|
| 14 | 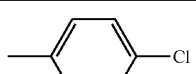 | 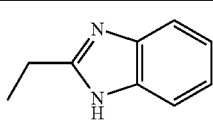 |  |
| 15 | 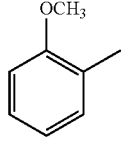 |  | 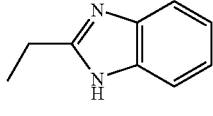 |
| 16 |  | 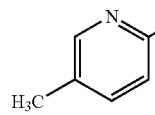 | 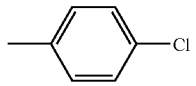 |
| 17 | 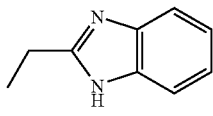 |  | 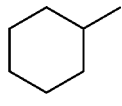 |
| 18 |  | 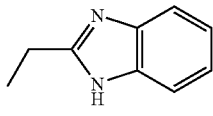 |  |
| 19 | 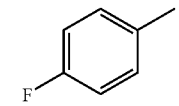 | 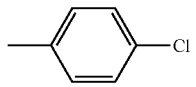 | 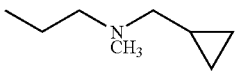 |
| 20 |  | 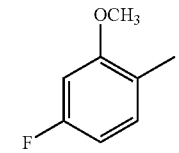 | 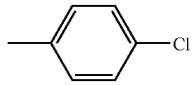 |
| 21 | 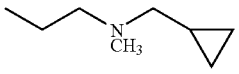 |  | 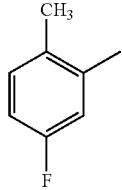 |

TABLE 1A-continued
| Cpd. No. | Ar¹ | R¹ | R² |
|---|---|---|---|
| 22 | 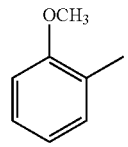 | 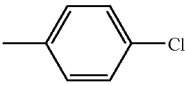 | 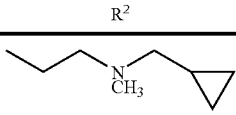 |
| 23 | 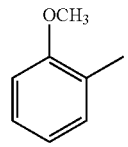 | 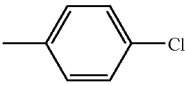 | 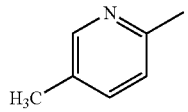 |
| 24 | 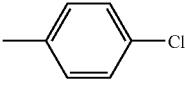 | 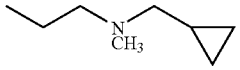 | 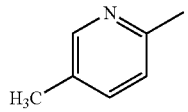 |
| 25 | 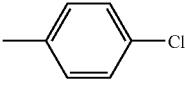 | 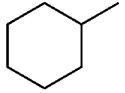 | 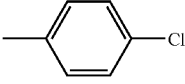 |
| 26 | 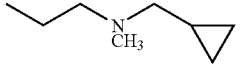 | 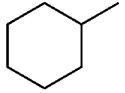 | 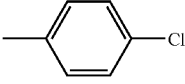 |
| 27 | 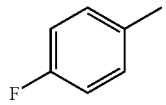 | 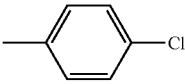 | 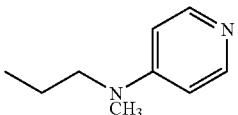 |
| 28 | 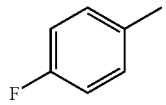 | 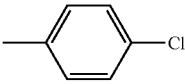 |  |
| 29 | 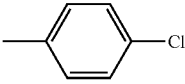 | 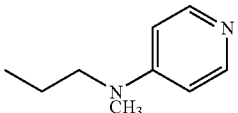 |  |
| 30 | 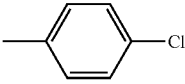 | 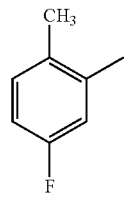 | 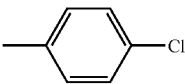 |

TABLE 1A-continued

| Cpd. No. | Ar¹ | R¹ | R² |
|---|---|---|---|
| 31 | cyclohexyl-methyl | 4-Cl-phenyl-methyl | propyl-N(CH₃)-(pyridin-4-yl) |
| 32 | 4-F-phenyl-methyl | 4-Cl-phenyl-methyl | -CH₂C(=O)O-CH₂CH₃ |
| 33 | 4-F-phenyl-methyl | 4-Cl-phenyl-methyl | propyl-NH-CH₂-cyclopropyl |
| 34 | 4-F-phenyl-methyl | 4-Cl-phenyl-methyl | propyl-N(CH₃)-cyclobutyl |
| 35 | 4-F-phenyl-methyl | 4-Cl-phenyl-methyl | propyl-NH-cyclobutyl |
| 36 | 4-F-phenyl-methyl | 4-Cl-phenyl-methyl | -CH₂C(=O)-pyrrolidin-1-yl |
| 37 | 4-F-phenyl-methyl | 4-Cl-phenyl-methyl | propyl-morpholin-4-yl |
| 38 | 4-F-phenyl-methyl | 4-Cl-phenyl-methyl | propyl-(4-methylpiperazin-1-yl) |
| 39 | 4-F-phenyl-methyl | 4-Cl-phenyl-methyl | -CH₂C(=O)NH-(4-F-phenyl) |
| 40 | 4-F-phenyl-methyl | 4-Cl-phenyl-methyl | propyl-NH-(4-F-phenyl) |
| 41 | 4-F-phenyl-methyl | 4-Cl-phenyl-methyl | -CH₂C(=O)N(CH₃)-(4-F-phenyl) |

TABLE 1A-continued

| Cpd. No. | Ar¹ | R¹ | R² |
|---|---|---|---|
| 42 | 4-F-C₆H₄ | 4-Cl-C₆H₄ | -CH₂CH₂C(O)NH-C₆H₄-4-OCH₃ |
| 43 | 4-F-C₆H₄ | 4-Cl-C₆H₄ | -CH₂CH₂CH₂NH-C₆H₄-4-OCH₃ |
| 44 | 4-F-C₆H₄ | 4-Cl-C₆H₄ | -CH₂CH₂C(O)N(CH₃)-C₆H₄-4-OCH₃ |
| 45 | 4-F-C₆H₄ | 4-Cl-C₆H₄ | -CH₂CH₂C(O)NH-(4-pyridyl) |
| 46 | 4-F-C₆H₄ | 4-Cl-C₆H₄ | -CH₂CH₂CH₂NH-(4-pyridyl) |
| 47 | 4-F-C₆H₄ | 4-Cl-C₆H₄ | -CH₂CH₂C(O)N(CH₃)-(4-pyridyl) |
| 48 | 4-F-C₆H₄ | 4-Cl-C₆H₄ | -CH₂CH₂C(O)NH-cyclohexyl |
| 49 | 4-F-C₆H₄ | 4-Cl-C₆H₄ | -CH₂CH₂CH₂NH-cyclohexyl |
| 50 | 4-F-C₆H₄ | 4-Cl-C₆H₄ | -CH₂CH₂C(O)N(CH₃)-cyclohexyl |
| 51 | 4-F-C₆H₄ | 4-Cl-C₆H₄ | 3-ethyl-5-phenyl-4H-1,2,4-triazol-yl |

TABLE 1A-continued

| Cpd. No. | Ar¹ | R¹ | R² |
|---|---|---|---|
| 52 | 4-F-phenyl | 4-Cl-phenyl | -CH₂CH₂-(4-OCH₃-phenyl) |
| 53 | 4-F-phenyl | 4-Cl-phenyl | -CH₂CH₂CH₂-O-(4-F-phenyl) |
| 54 | 4-F-phenyl | 4-Cl-phenyl | -CH₂C(O)-(4-OCH₃-phenyl) |
| 55 | 4-F-phenyl | 4-Cl-phenyl | -CH₂CH₂-cyclohexyl |
| 56 | 4-F-phenyl | 4-Cl-phenyl | -CH₂CH₂CH₂-pyrrolidin-1-yl |
| 57 | 4-F-phenyl | 4-Cl-phenyl | -CH₂CH₂CH₂-piperidin-1-yl |
| 58 | 4-F-phenyl | 4-Cl-phenyl | -CH₂CH₂CH₂-N(CH₃)-(4-F-phenyl) |
| 59 | 4-F-phenyl | 4-Cl-phenyl | -CH₂CH₂CH₂-N(CH₃)-(4-OCH₃-phenyl) |
| 60 | 4-F-phenyl | 4-Cl-phenyl | -CH₂CH₂CH₂-N(CH₃)-cyclohexyl |
| 61 | 4-F-phenyl | 4-Cl-phenyl | -CH₂-(1-methyl-1H-benzimidazol-2-yl) |
| 62 | 4-F-phenyl | 4-Cl-phenyl | -CH₂-(benzothiazol-2-yl) |

TABLE 1A-continued

| Cpd. No. | Ar¹ | R¹ | R² |
|---|---|---|---|
| 63 | 4-F-phenyl | 4-Cl-phenyl | 2-(1H-imidazol-2-yl)ethyl |
| 64 | 4-F-phenyl | 4-Cl-phenyl | 2-(thiazol-2-yl)ethyl |
| 65 | 4-F-phenyl | 4-Cl-phenyl | 2-(pyridin-2-yl)ethyl |
| 66 | 4-F-phenyl | 4-Cl-phenyl | 2-(pyridin-3-yl)ethyl |
| 67 | 4-F-phenyl | 4-Cl-phenyl | 2-(pyridin-4-yl)ethyl |
| 68 | 4-F-2-OCH₃-phenyl | 4-Cl-phenyl | 3-(pyrrolidin-1-yl)propyl |
| 69 | 4-F-2-OCH₃-phenyl | 4-Cl-phenyl | 3-(piperidin-1-yl)propyl |
| 70 | 4-F-2-OCH₃-phenyl | 4-Cl-phenyl | 3-[N-methyl-N-(4-fluorophenyl)amino]propyl |
| 71 | 4-F-2-OCH₃-phenyl | 4-Cl-phenyl | 3-[N-methyl-N-(4-methoxyphenyl)amino]propyl |
| 72 | 4-F-2-OCH₃-phenyl | 4-Cl-phenyl | 3-[N-methyl-N-cyclohexylamino]propyl |

TABLE 1A-continued

| Cpd. No. | Ar¹ | R¹ | R² |
| --- | --- | --- | --- |
| 73 | 4-F, 2-OCH₃, 1-methyl phenyl | 4-Cl-phenyl | 2-ethyl-1-methyl-1H-benzimidazole |
| 74 | 4-F, 2-OCH₃, 1-methyl phenyl | 4-Cl-phenyl | 2-ethyl-benzothiazole |
| 75 | 4-F, 2-OCH₃, 1-methyl phenyl | 4-Cl-phenyl | 2-ethyl-1H-imidazole |
| 76 | 4-F, 2-OCH₃, 1-methyl phenyl | 4-Cl-phenyl | 2-ethyl-thiazole |
| 77 | 4-F, 2-OCH₃, 1-methyl phenyl | 4-Cl-phenyl | 5-ethyl-2-methyl-thiazole |
| 78 | 4-F, 2-OCH₃, 1-methyl phenyl | 4-Cl-phenyl | 2-ethyl-pyridine |
| 79 | 4-F, 2-OCH₃, 1-methyl phenyl | 4-Cl-phenyl | 3-ethyl-pyridine |
| 80 | 4-F, 2-OCH₃, 1-methyl phenyl | 4-Cl-phenyl | 4-ethyl-pyridine |

TABLE 1A-continued
| Cpd. No. | Ar¹ | R¹ | R² |
|---|---|---|---|
| 81 | 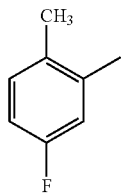 | 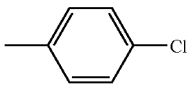 | 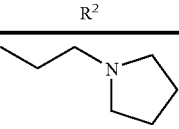 |
| 82 | 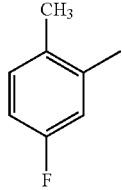 | 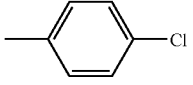 | 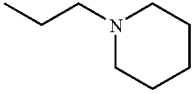 |
| 83 | 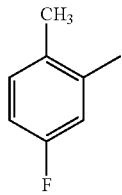 | 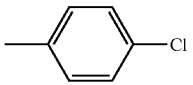 | 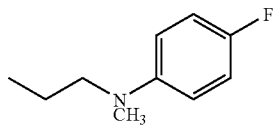 |
| 84 | 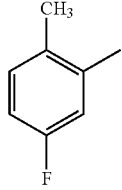 | 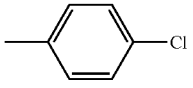 | 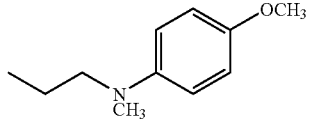 |
| 85 | 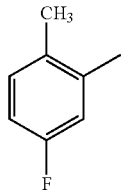 | 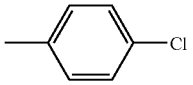 | 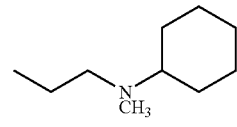 |
| 86 | 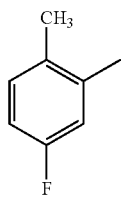 | 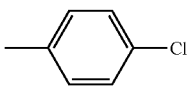 | 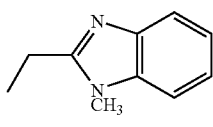 |
| 87 | 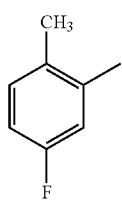 | 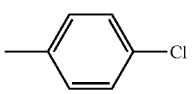 | 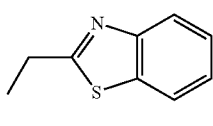 |

TABLE 1A-continued
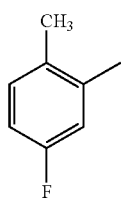
| Cpd. No. | Ar¹ | R¹ | R² |
|---|---|---|---|
| 88 | 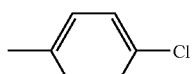 | 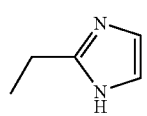 | 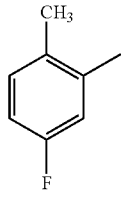 |
| 89 |  | 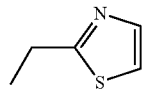 | 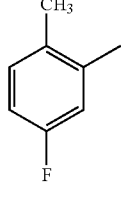 |
| 90 | 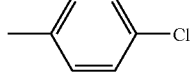 | 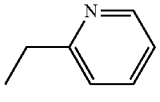 | 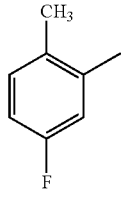 |
| 91 |  | 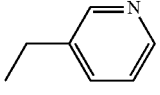 | 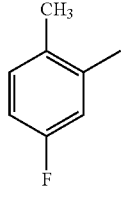 |
| 92 | 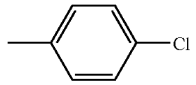 | 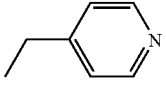 | 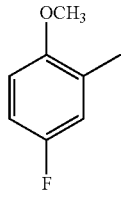 |
| 93 |  | 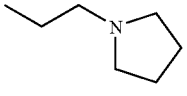 | |

TABLE 1A-continued
| Cpd. No. | Ar¹ | R¹ | R² |
|---|---|---|---|
| 94 | 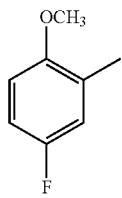 | 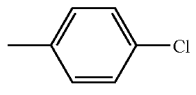 | 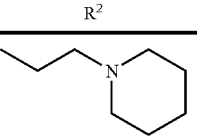 |
| 95 | 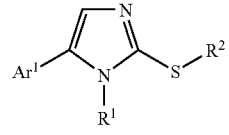 |  | 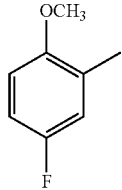 |
| 96 | 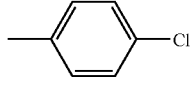 | 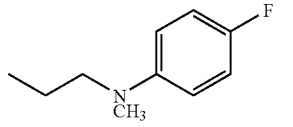 | 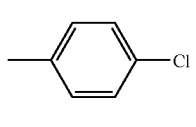 |
| 97 | 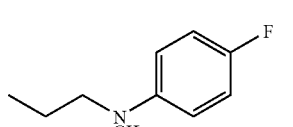 | 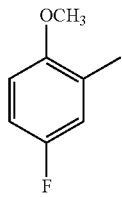 | 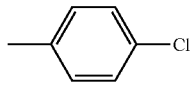 |
| 98 | 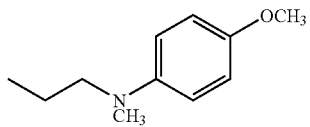 | 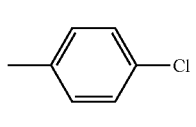 | 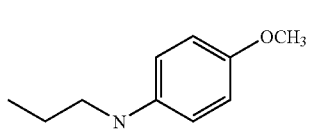 |
| 99 | 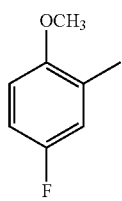 | 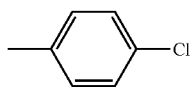 | 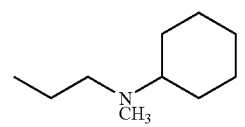 |
| 100 | 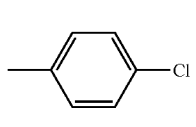 | 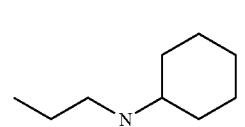 | 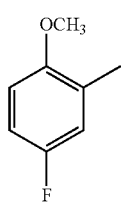 |

TABLE 1A-continued
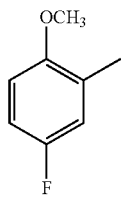
| Cpd. No. | Ar¹ | R¹ | R² |
|---|---|---|---|
| 101 | 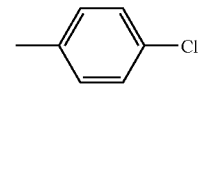 | 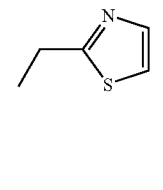 | 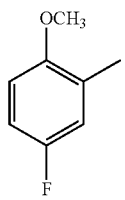 |
| 102 | 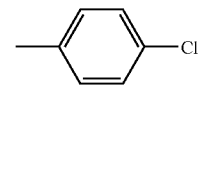 | 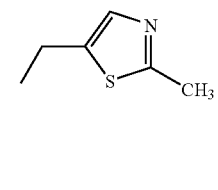 | 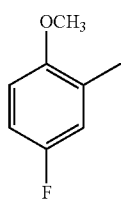 |
| 103 | 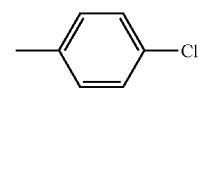 | 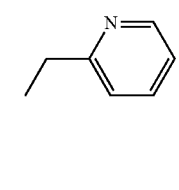 | 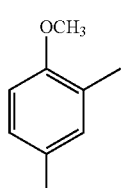 |
| 104 | 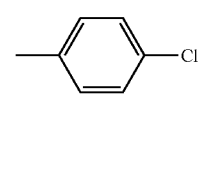 | 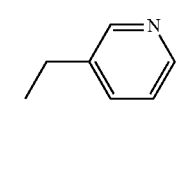 | 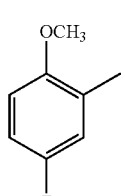 |
| 105 | 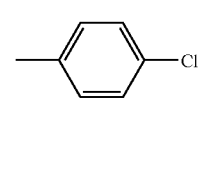 | 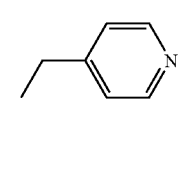 | 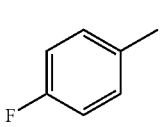 |
| 106 | 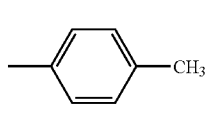 | 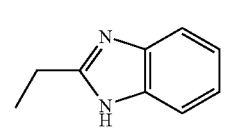 | 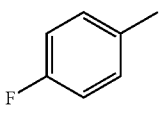 |
| 107 | 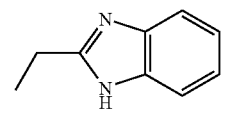 | CH₃ | 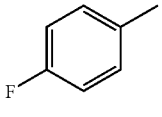 |
| 108 | 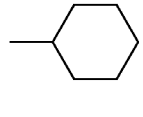 | 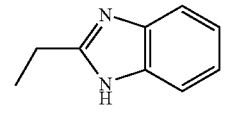 |  |

TABLE 1A-continued
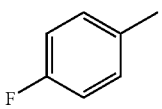
| Cpd. No. | Ar¹ | R¹ | R² |
|---|---|---|---|
| 109 | 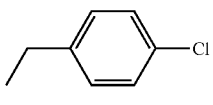 | 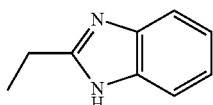 | 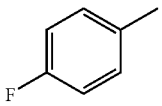 |
| 110 | 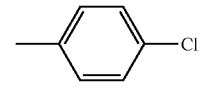 | 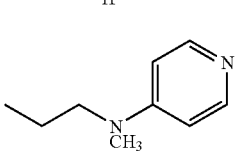 | 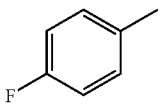 |
| 111 | 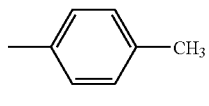 | 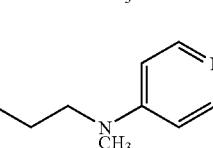 | 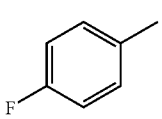 |
| 112 | 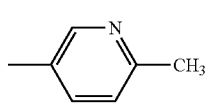 | 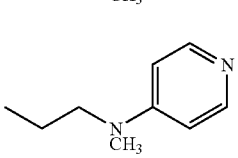 | 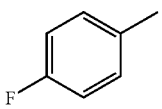 |
| 113 | 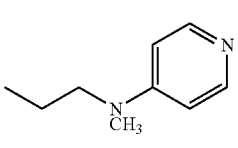 | CH₃ | 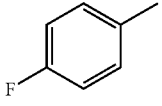 |
| 114 | 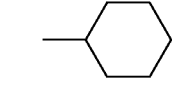 | 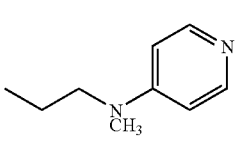 | 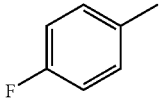 |
| 115 | 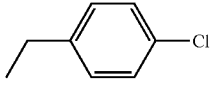 | 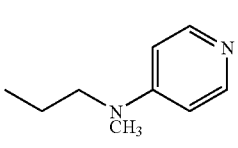 | 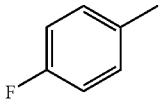 |
| 116 | 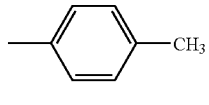 | 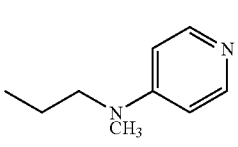 | 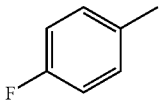 |
| 117 | 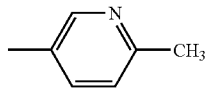 | 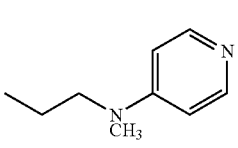 | 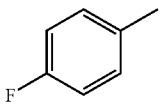 |
| 118 | 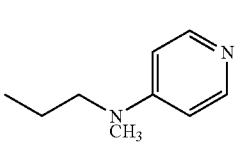 | CH₃ | |

TABLE 1A-continued
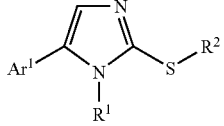
| Cpd. No. | Ar¹ | R¹ | R² |
| --- | --- | --- | --- |
| 119 | 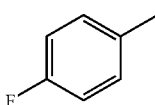 | 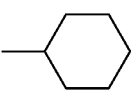 | 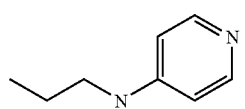 |
| 120 | 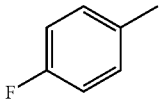 | 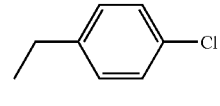 | 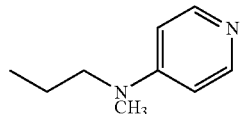 |
TABLE 1B
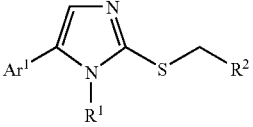
| Cpd. No. | Ar¹ | R¹ | R² |
| --- | --- | --- | --- |
| 121 | 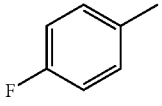 | 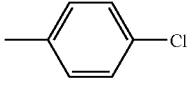 | 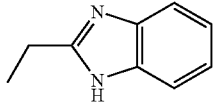 |
| 122 |  | 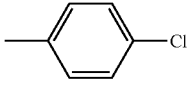 | 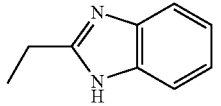 |
| 123 | 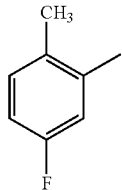 | 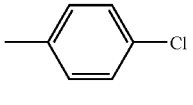 | 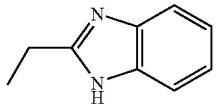 |
| 124 | 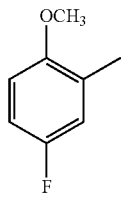 | 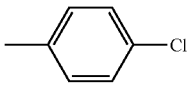 | 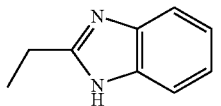 |
| 125 | 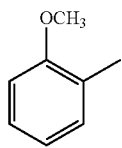 | 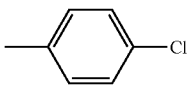 | 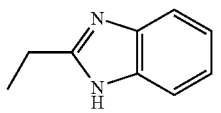 |

TABLE 1B-continued

| Cpd. No. | Ar¹ | R¹ | R² |
|---|---|---|---|
| 126 | 5-methyl-pyridin-2-yl | 4-Cl-phenyl | 2-ethyl-1H-benzimidazol-yl |
| 127 | cyclohexyl | 4-Cl-phenyl | 2-ethyl-1H-benzimidazol-yl |
| 128 | 4-F-phenyl | 4-Cl-phenyl | N(CH₃)CH₂-cyclopropyl propyl |
| 129 | 2-OCH₃-4-F-phenyl | 4-Cl-phenyl | N(CH₃)CH₂-cyclopropyl propyl |
| 130 | 2-CH₃-4-F-phenyl | 4-Cl-phenyl | N(CH₃)CH₂-cyclopropyl propyl |
| 131 | 2-CH₃-4-F-OCH₃-phenyl | 4-Cl-phenyl | N(CH₃)CH₂-cyclopropyl propyl |
| 132 | 2-OCH₃-phenyl | 4-Cl-phenyl | N(CH₃)CH₂-cyclopropyl propyl |
| 133 | 5-methyl-pyridin-2-yl | 4-Cl-phenyl | N(CH₃)CH₂-cyclopropyl propyl |
| 134 | cyclohexyl | 4-Cl-phenyl | N(CH₃)CH₂-cyclopropyl propyl |

TABLE 1B-continued

[Structure: Ar¹-substituted imidazole with N-R¹ and S-CH₂-R² at position 2]

| Cpd. No. | Ar¹ | R¹ | R² |
|---|---|---|---|
| 135 | 4-fluorophenyl | 4-chlorophenyl | -CH₂CH₂-N(CH₃)-(pyridin-4-yl) |
| 136 | 2-methoxy-4-fluorophenyl | 4-chlorophenyl | -CH₂CH₂-N(CH₃)-(pyridin-4-yl) |
| 137 | 2-methyl-4-fluorophenyl | 4-chlorophenyl | -CH₂CH₂-N(CH₃)-(pyridin-4-yl) |
| 138 | 2-methoxy-4-fluorophenyl (OCH₃ ortho, CH₃ meta) | 4-chlorophenyl | -CH₂CH₂-N(CH₃)-(pyridin-4-yl) |
| 139 | 2-methoxyphenyl | 4-chlorophenyl | -CH₂CH₂-N(CH₃)-(pyridin-4-yl) |
| 140 | 5-methylpyridin-2-yl | 4-chloropyridin-?-yl | -CH₂CH₂-N(CH₃)-(pyridin-4-yl) |
| 141 | cyclohexyl | 4-chlorophenyl | -CH₂CH₂-N(CH₃)-(pyridin-4-yl) |
| 142 | 4-fluorophenyl | 4-chlorophenyl | -CH₂C(O)OCH₂CH₃ |
| 143 | 4-fluorophenyl | 4-chlorophenyl | -CH₂CH₂-NH-CH₂-cyclopropyl |

TABLE 1B-continued
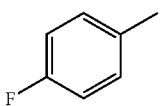
| Cpd. No. | Ar¹ | R¹ | R² |
| --- | --- | --- | --- |
| 144 | 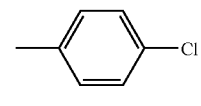 | 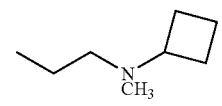 | 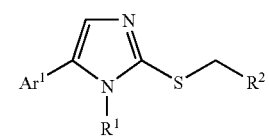 |
| 145 | 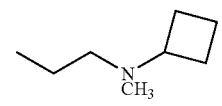 | 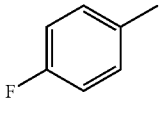 | 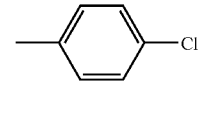 |
| 146 | 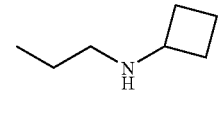 | 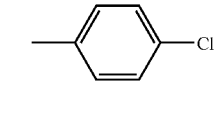 | 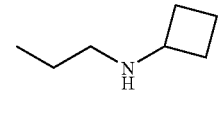 |
| 147 | 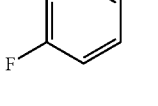 | 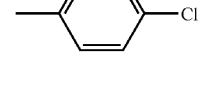 | 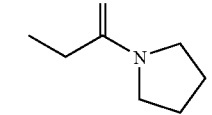 |
| 148 | 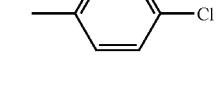 | 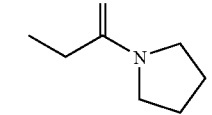 | 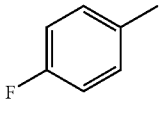 |
| 149 | 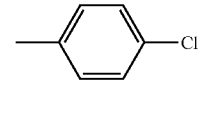 | 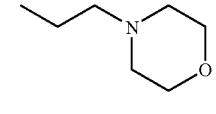 | 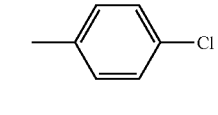 |
| 150 | 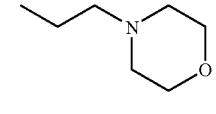 | 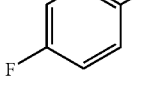 | 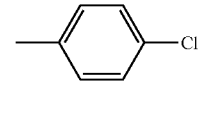 |
| 151 | 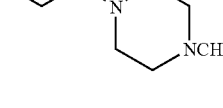 | 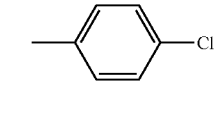 | 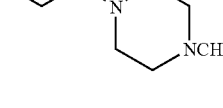 |
| 152 | 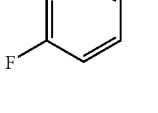 | 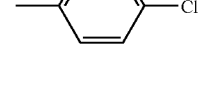 | 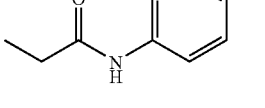 |
| 153 | 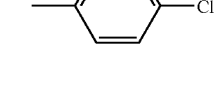 | 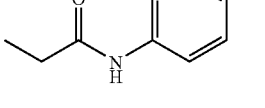 | 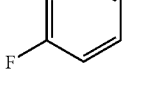 |

TABLE 1B-continued
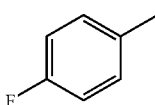
| Cpd. No. | Ar¹ | R¹ | R² |
|---|---|---|---|
| 154 | 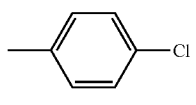 | 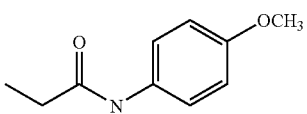 | 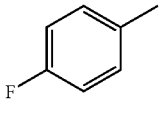 |
| 155 | 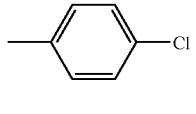 | 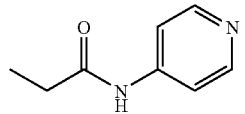 | 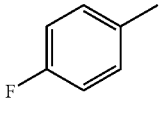 |
| 156 | 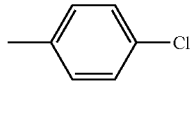 | 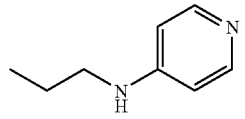 | 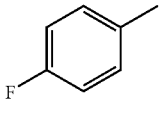 |
| 157 | 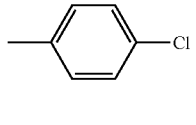 | 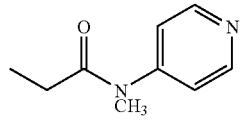 | 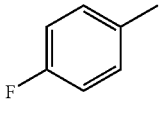 |
| 158 | 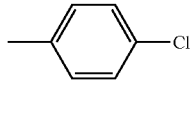 | 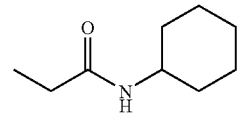 | 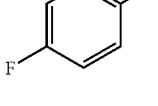 |
| 159 | 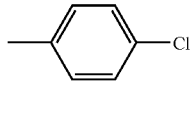 | 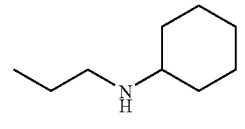 | 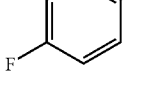 |
| 160 | 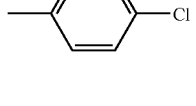 | 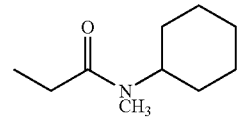 | 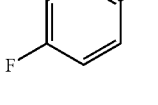 |
| 161 | 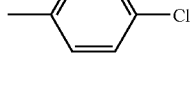 | 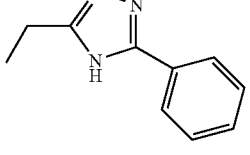 | 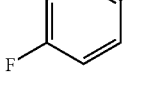 |
| 162 | 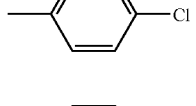 | 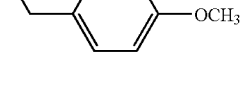 | 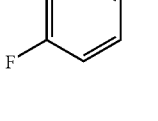 |
| 163 | 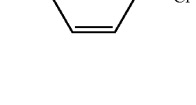 | 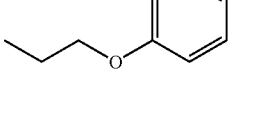 | |

TABLE 1B-continued
| Cpd. No. | Ar¹ | R¹ | R² |
|---|---|---|---|
| 164 | 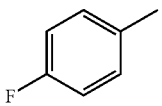 | 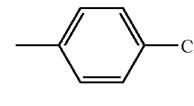 | 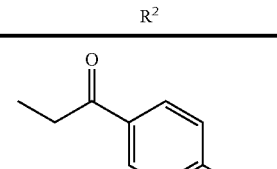 |
| 165 | 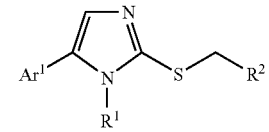 | 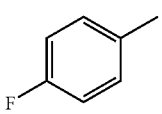 | 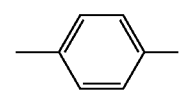 |
| 166 | 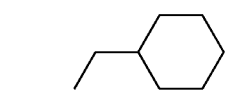 | 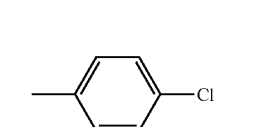 | 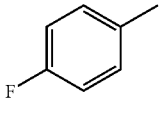 |
| 167 | 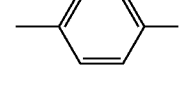 | 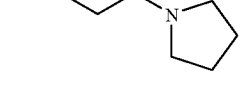 | 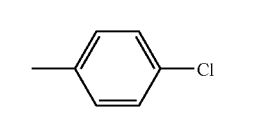 |
| 168 | 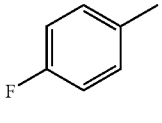 | 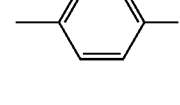 | 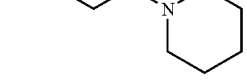 |
| 169 | 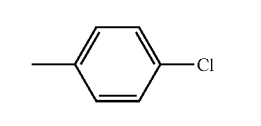 | 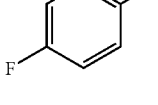 | 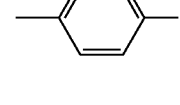 |
| 170 | 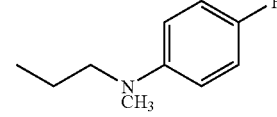 | 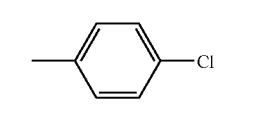 | 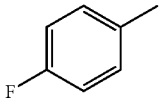 |
| 171 | 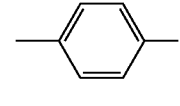 | 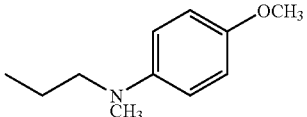 | 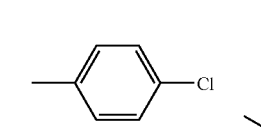 |
| 172 | 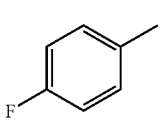 | 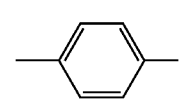 | 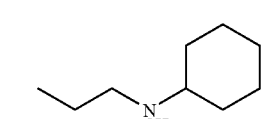 |
| 173 | 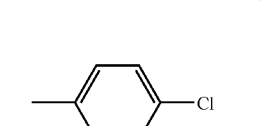 | 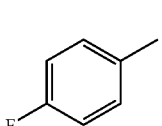 | 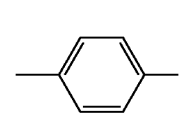 |
| 174 | 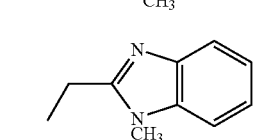 | 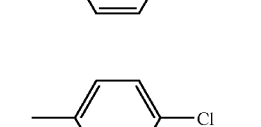 | 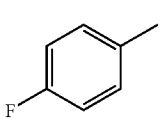 |

TABLE 1B-continued
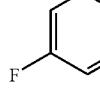
| Cpd. No. | Ar¹ | R¹ | R² |
|---|---|---|---|
| 175 | 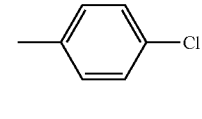 | 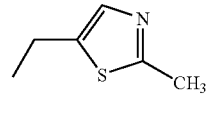 | 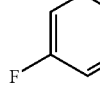 |
| 176 | 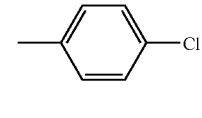 | 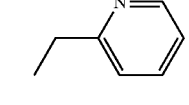 | 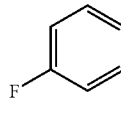 |
| 177 | 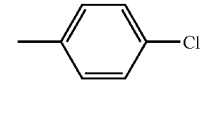 | 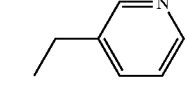 | 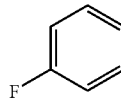 |
| 178 | 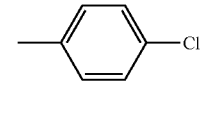 | 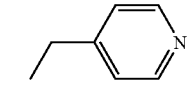 | 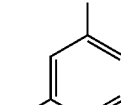 |
| 179 | 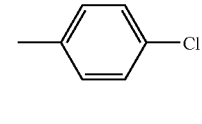 | 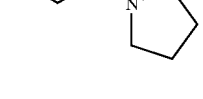 | 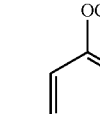 |
| 180 | 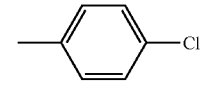 | 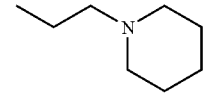 | 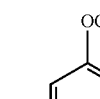 |
| 181 | 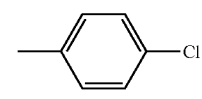 | 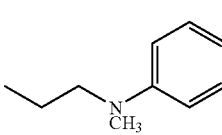 | 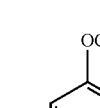 |
| 182 | 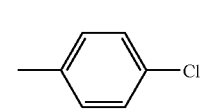 |  | 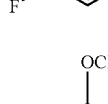 |
| 183 | 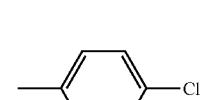 |  | |

TABLE 1B-continued

| Cpd. No. | Ar¹ | R¹ | R² |
|---|---|---|---|
| 184 | 5-fluoro-2-methyl-phenyl with 2-OCH₃ | 4-Cl-phenyl | 2-ethyl-1-methyl-benzimidazole |
| 185 | 5-fluoro-2-methyl-phenyl with 2-OCH₃ | 4-Cl-phenyl | 2-ethyl-benzothiazole |
| 186 | 5-fluoro-2-methyl-phenyl with 2-OCH₃ | 4-Cl-phenyl | 2-ethyl-1H-imidazole |
| 187 | 5-fluoro-2-methyl-phenyl with 2-OCH₃ | 4-Cl-phenyl | 2-ethyl-thiazole |
| 188 | 5-fluoro-2-methyl-phenyl with 2-OCH₃ | 4-Cl-phenyl | 5-ethyl-2-methyl-thiazole |
| 189 | 5-fluoro-2-methyl-phenyl with 2-OCH₃ | 4-Cl-phenyl | 2-ethyl-pyridine |
| 190 | 5-fluoro-2-methyl-phenyl with 2-OCH₃ | 4-Cl-phenyl | 3-ethyl-pyridine |
| 191 | 5-fluoro-2-methyl-phenyl with 2-OCH₃ | 4-Cl-phenyl | 4-ethyl-pyridine |

TABLE 1B-continued
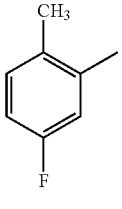
| Cpd. No. | Ar¹ | R¹ | R² |
|---|---|---|---|
| 192 | 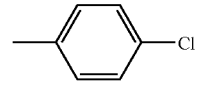 | 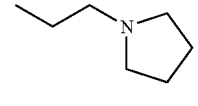 | 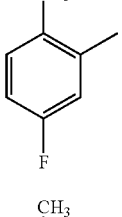 |
| 193 | 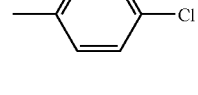 | 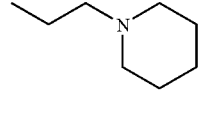 | 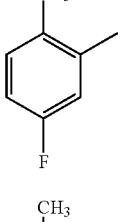 |
| 194 | 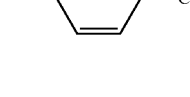 | 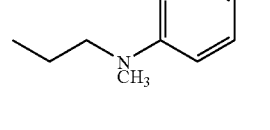 | 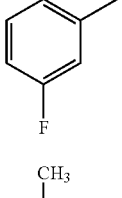 |
| 195 | 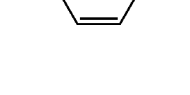 | 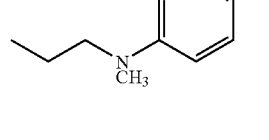 | 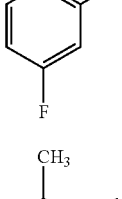 |
| 196 |  | 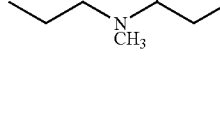 | 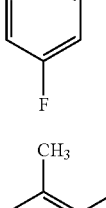 |
| 197 |  | 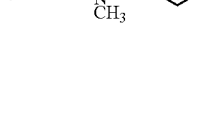 | 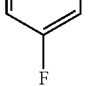 |
| 198 |  | |  |

TABLE 1B-continued
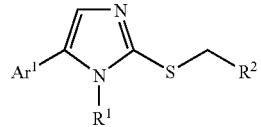
| Cpd. No. | Ar¹ | R¹ | R² |
|---|---|---|---|
| 199 | 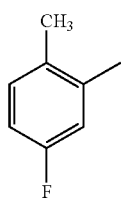 | 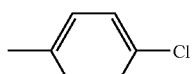 | 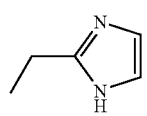 |
| 200 | 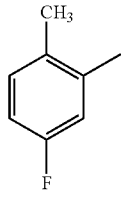 |  | 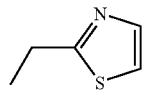 |
| 201 | 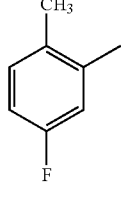 | 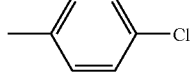 | 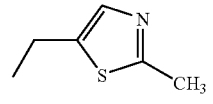 |
| 202 | 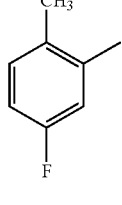 | 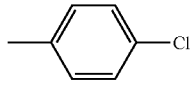 | 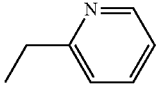 |
| 203 | 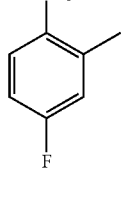 | 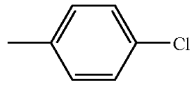 | 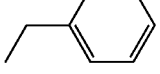 |
| 204 | 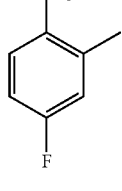 | 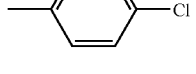 | 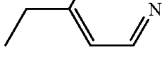 |

TABLE 1B-continued

Ar¹—[imidazole core]—S—CH₂—R²
       |
       R¹

| Cpd. No. | Ar¹ | R¹ | R² |
| --- | --- | --- | --- |
| 205 | 4-fluoro-2-methyl-1-methoxyphenyl | 4-chlorophenyl | propyl-pyrrolidin-1-yl |
| 206 | 4-fluoro-2-methyl-1-methoxyphenyl | 4-chlorophenyl | propyl-piperidin-1-yl |
| 207 | 4-fluoro-2-methyl-1-methoxyphenyl | 4-chlorophenyl | N-methyl-N-(4-fluorophenyl)propyl |
| 208 | 4-fluoro-2-methyl-1-methoxyphenyl | 4-chlorophenyl | N-methyl-N-(4-methoxyphenyl)propyl |
| 209 | 4-fluoro-2-methyl-1-methoxyphenyl | 4-chlorophenyl | N-methyl-N-cyclohexylpropyl |
| 210 | 4-fluoro-2-methyl-1-methoxyphenyl | 4-chlorophenyl | 2-ethyl-1-methylbenzimidazole |
| 211 | 4-fluoro-2-methyl-1-methoxyphenyl | 4-chlorophenyl | 2-ethylbenzothiazole |

TABLE 1B-continued
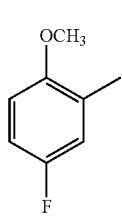
| Cpd. No. | Ar¹ | R¹ | R² |
|---|---|---|---|
| 212 | 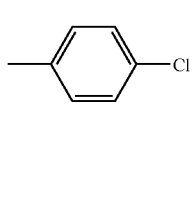 | 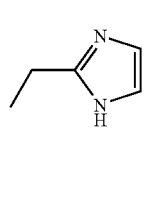 | 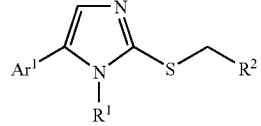 |
| 213 | 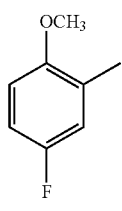 | 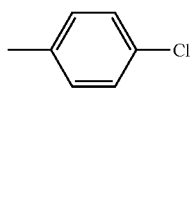 | 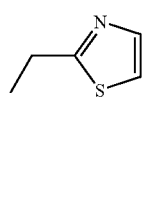 |
| 214 | 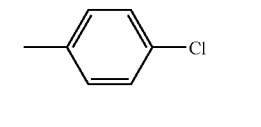 | 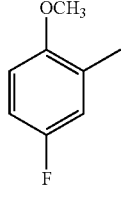 | 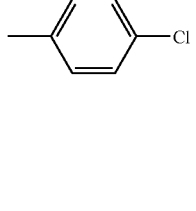 |
| 215 | 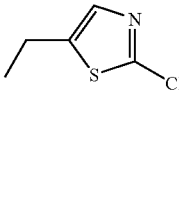 | 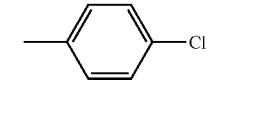 | 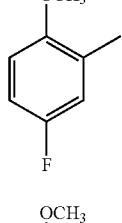 |
| 216 | 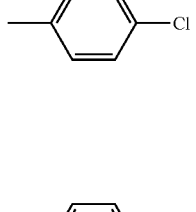 | 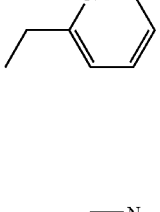 | 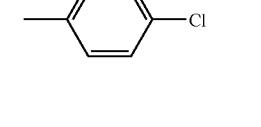 |
| 217 | 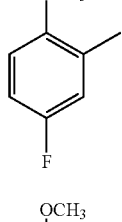 | 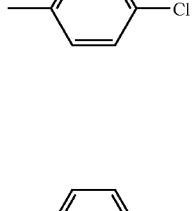 | 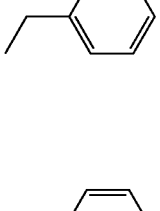 |
| 218 | 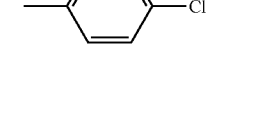 | 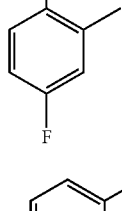 | 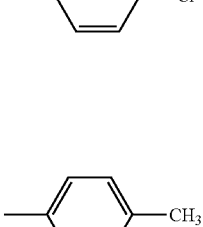 |

TABLE 1B-continued
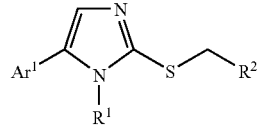
| Cpd. No. | Ar¹ | R¹ | R² |
|---|---|---|---|
| 219 | 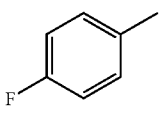 | 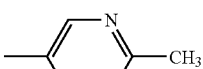 | 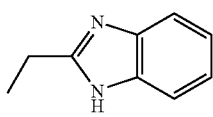 |
| 220 | 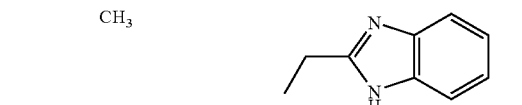 | CH₃ | 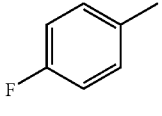 |
| 221 | 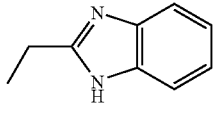 | 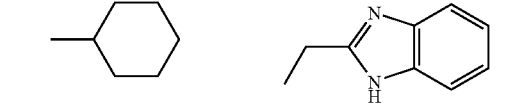 | 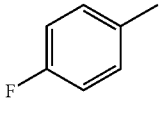 |
| 222 | 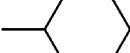 | 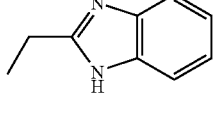 | 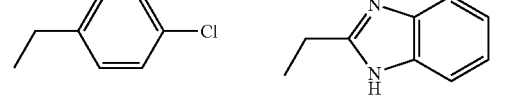 |
| 223 | 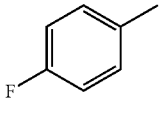 | 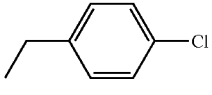 | 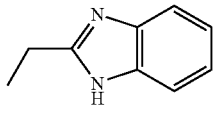 |
| 224 | 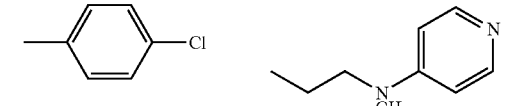 | 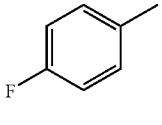 | 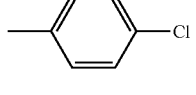 |
| 225 | 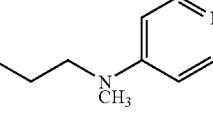 | 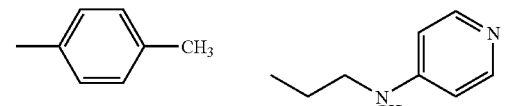 | 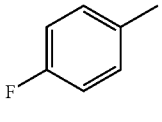 |
| 226 | 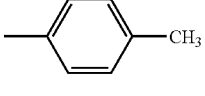 | CH₃ | 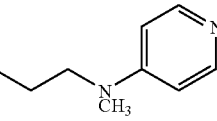 |
| 227 | 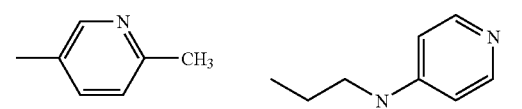 | 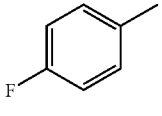 | 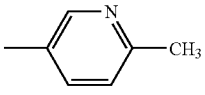 |
| 228 | 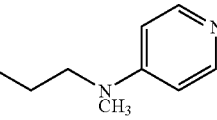 | 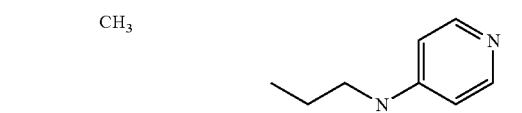 | 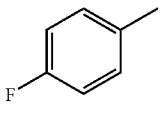 |

TABLE 1B-continued

![structure: Ar¹-imidazole-N(R¹)-S-CH2-R²]

| Cpd. No. | Ar¹ | R¹ | R² |
|---|---|---|---|
| 229 | 4-F-phenyl | 4-methylphenyl (p-tolyl) | -CH2CH2-N(CH3)-(pyridin-4-yl) |
| 230 | 4-F-phenyl | 6-methylpyridin-3-yl | -CH2CH2-N(CH3)-(pyridin-4-yl) |
| 231 | 4-F-phenyl | CH3 | -CH2CH2-N(CH3)-(pyridin-4-yl) |
| 232 | 4-F-phenyl | cyclohexyl | -CH2CH2-N(CH3)-(pyridin-4-yl) |
| 233 | 4-F-phenyl | 4-Cl-phenylethyl | -CH2CH2-N(CH3)-(pyridin-4-yl) |

TABLE 1C

![structure: Ar¹-imidazole-N(R¹)-S-R²]

| Cpd No. | Ar¹ | R¹ | R² |
|---|---|---|---|
| 234 | 4-F-phenyl | 4-methoxyphenyl | -CH2CH2-C(O)-NH-CH2-(furan-2-yl) |
| 235 | 4-F-phenyl | CH3 | -CH2CH2-C(O)-NH-(4-F-phenyl) |
| 236 | phenyl | CH3 | -CH2CH2-C(O)-N(CH2CH3)2 |

TABLE 1C-continued
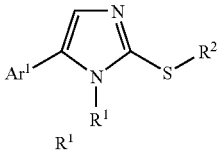
| Cpd No. | Ar¹ | R¹ | R² |
|---|---|---|---|
| 237 | 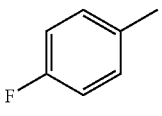 | CH₃ | 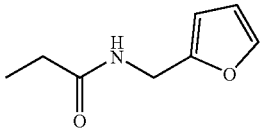 |
| 238 | 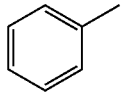 | CH₃ | 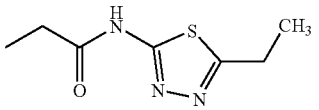 |
| 239 | 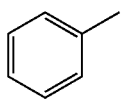 | Et | 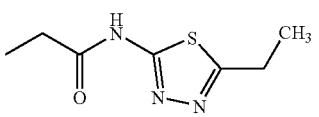 |
| 240 | 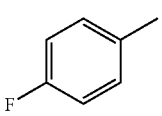 | CH₃ | 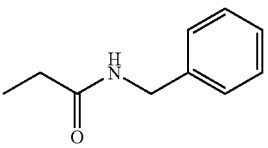 |
| 241 | 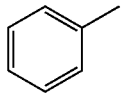 | CH₃ | 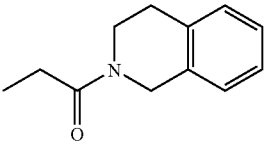 |
| 242 | 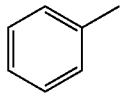 | CH₃ | 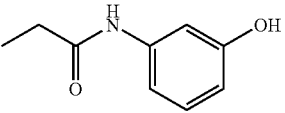 |
| 243 | 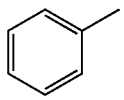 | 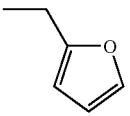 | 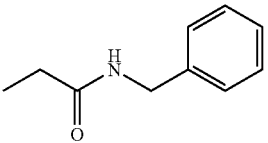 |
| 244 | 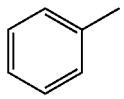 | CH₃ | 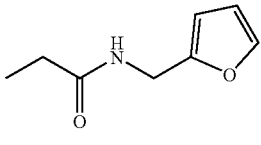 |
| 245 | 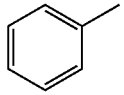 | CH₃ | 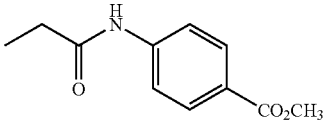 |
| 246 | 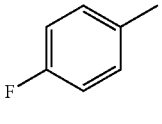 | 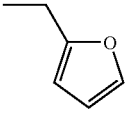 | 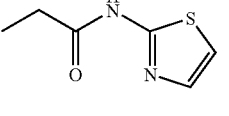 |

TABLE 1C-continued
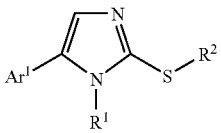
| Cpd No. | Ar¹ | R¹ | R² |
|---|---|---|---|
| 247 | 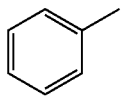 | 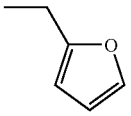 | 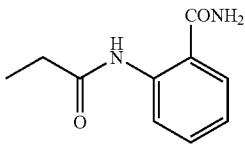 |
| 248 | 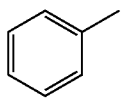 | 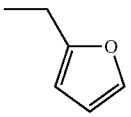 | 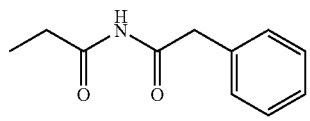 |
| 249 | 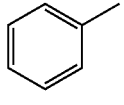 | 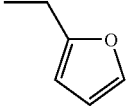 | 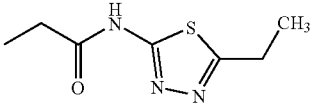 |
| 250 | 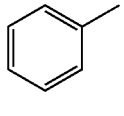 | CH₃ | 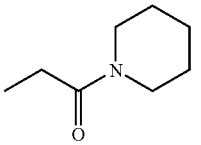 |
| 251 | 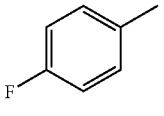 | CH₃ | 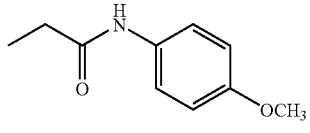 |
| 252 | 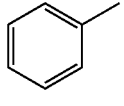 | Et | 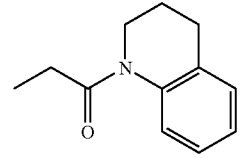 |
| 253 | 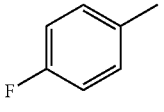 | CH₃ | 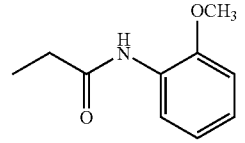 |
| 254 | 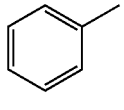 | CH₃ | 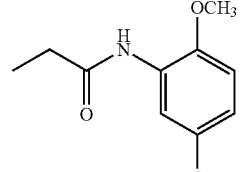 |
| 255 | 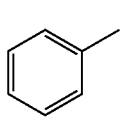 | CH₃ | 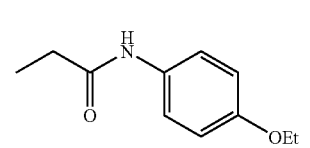 |

TABLE 1C-continued
| Cpd No. | Ar¹ | R¹ | R² |
|---|---|---|---|
| 256 | 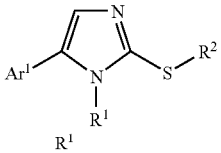 | CH₃ | 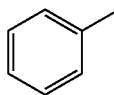 |
| 257 | 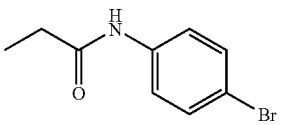 | CH₃ | 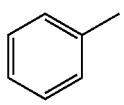 |
| 258 | 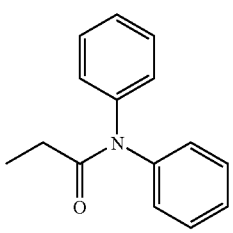 | CH₃ | 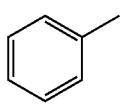 |
| 259 | 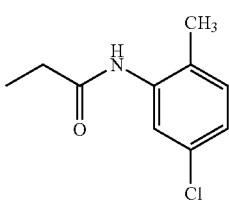 | CH₃ | 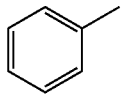 |
| 260 | 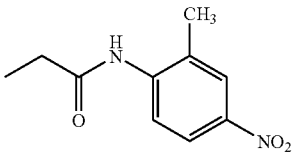 | CH₃ | 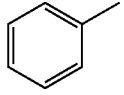 |
| 261 | 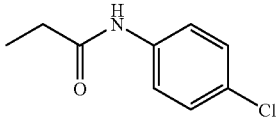 | Et | 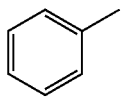 |
| 262 | 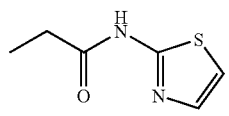 | CH₃ | 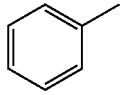 |
| 263 | 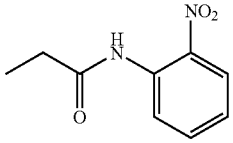 | 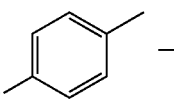 | 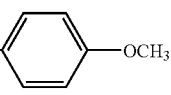 |
| 264 | 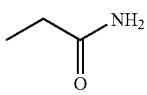 | 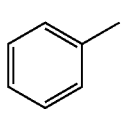 | 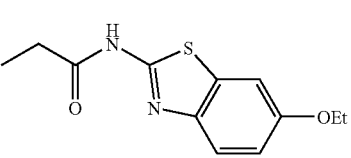 |

TABLE 1C-continued
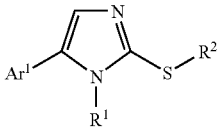
| Cpd No. | Ar¹ | R¹ | R² |
|---|---|---|---|
| 265 | 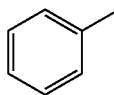 | 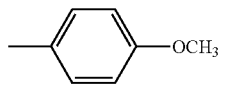 | 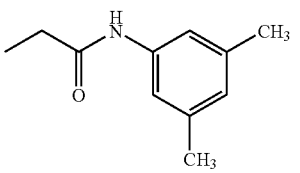 |
| 266 | 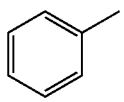 | 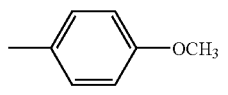 | 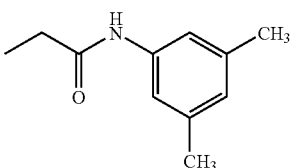 |
| 267 | 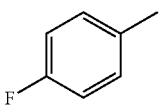 | 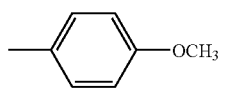 | 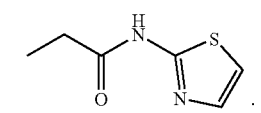 |
13. A composition comprising a compound of formula I, or pharmaceutically acceptable salt thereof, according to any one of claims 1-12 and a pharmaceutically acceptable carrier.
14. The composition of claim 13, further comprising an additional therapeutic agent.
* * * * *